United States Patent [19]

Williams et al.

[11] 4,239,351
[45] Dec. 16, 1980

[54] APPARATUS FOR GENERATING AND DISPLAYING VISUAL ACUITY TARGETS

[75] Inventors: Robert E. Williams, Pearland; Thomas A. Decker, Houston; Charles Kurtzman, Houston; Christian L. Kuether, Houston, all of Tex.

[73] Assignee: Baylor College of Medicine, Houston, Tex.

[21] Appl. No.: 945,943

[22] Filed: Sep. 26, 1978

[51] Int. Cl.³ .............................................. A61B 3/02
[52] U.S. Cl. ........................................ 351/36; 351/17
[58] Field of Search ..................... 351/17, 30, 32, 36, 351/23, 24, 39

[56] References Cited

U.S. PATENT DOCUMENTS

| Re. 28,921 | 8/1976 | Haines et al. | 351/30 X |
|---|---|---|---|
| 2,564,794 | 8/1951 | Shekels | 351/23 X |
| 3,517,988 | 6/1970 | Schwiad | 351/30 |
| 3,639,042 | 2/1972 | Grolman | 351/30 |
| 3,684,355 | 8/1972 | Molner | 351/36 |
| 3,705,003 | 12/1972 | Lynn et al. | 351/36 X |
| 3,737,217 | 6/1973 | Haines et al. | 351/30 X |
| 3,883,235 | 5/1975 | Lynn et al. | 351/39 |
| 3,905,688 | 9/1975 | Decker | 351/30 |
| 3,969,020 | 7/1976 | Lynn et al. | 351/17 |
| 3,982,828 | 9/1976 | Woolf | 351/17 X |

OTHER PUBLICATIONS

Edward Crossman et al., "A Computer . . . Acuity", Amer. J. Optom & Arch. Amer. Acad. Optom., vol. 47, No. 5, May, 1970, pp. 344-355.

Primary Examiner—Paul A. Sacher
Attorney, Agent, or Firm—Fulbright & Jaworski

[57] ABSTRACT

First and second electro-optical display devices for displaying visual acuity targets, one of which is adapted to be viewed by a patient and the other of which is adapted to be viewed by an examiner. An electronic memory is connected to the display devices containing a plurality of acuity targets stored in various orientations for presentation to the display devices. Controls are provided in an examiner's console for selecting one of a plurality of available target sizes, "zoom" increasing size or decreasing size, selecting a single or a line of multiple target characters, providing normal or reverse video presentation, changing the orientation of the target characters, and providing a blank screen. The size of the targets is varied by changing the dimensions of each of the targets about its own center and in the case of multiple targets, maintaining proportional spacing between the targets as the size of the targets vary. A control console display indicates the size of the target displayed on the display devices. The orientation control prevents identical orientation of target characters on successive presentations. A beam splitter and hood assembly are positioned in front of the patient's display device for minimizing the effects of light reflections and ambient illumination.

23 Claims, 20 Drawing Figures

APPARATUS FOR GENERATING AND DISPLAYING VISUAL ACUITY TARGETS

BACKGROUND OF THE INVENTION

The invention relates to opthalmic testing instruments and more particularly to a device for measurement of visual acuity.

Typical clinical methods for measuring acuity involve the use of wall charts containing a fixed array of Snellen letters, Tumbling E targets or other accepted acuity targets. The patient ordinarily views the charts from a fixed distance (usually 20 feet). A second method in common use involves the projection of targets onto screens placed at a fixed distance by means of an optical system. Other methods, such as rear illuminated fixed target displays and motorized projectors utilizing a fixed series of target slide materials are also used.

The determination of visual acuity is an essential part of every eye examination. During the course of such an examination, acuity may be measured repeatedly to ascertain the resolution of each eye independently and both eyes together. The examination may also consist of independent and combined testing of the eyes with the aid of corrective lenses. In fact, the repeated determination of acuity forms an essential part of the process of refracting or determining the optimal corrective lenses to alleviate ametropia as well as a means for assessing the progress of ocular patholgy.

The methods and devices described above and presently in use have inherent defects and inadequacies which affect the validity of the data and the productivity of the examiner.

For example, memorization of the target materials by the patient is known to be one problem affecting the ability of the clinician to ascertain the patient's acuity. Acuity measurement devices which present a fixed array of targets are easily memorized, either voluntarily or involuntarily.

While not considered to be a critical aspect of testing, the inability to test acuity in small increments between standard target testing sizes is viewed as a restriction in most presently used methods.

The effect of ambient light upon the luminance and contrast of the projected type displays is considered a limitation because it requires that acuity be tested in reduced illumination. Hence the acuity of some patients measured in the clinic may differ considerably from their acuity in non-clinical environments.

The inability of known devices to provide white on black as well as black on white targets, to more adequately test low vision patients, is considered to be a disadvantage. The inability to present a single or multiple targets to compare "crowded" to "uncrowded" acuity for the detection of early amblyopes is a further disadvantage.

Finally, time has become a critical resource for the practitioner. The time required to instruct the patient regarding the target he is to view, or the time the clinician requires to find, adjust and align the required target in the case of projection devices becomes increasingly important with heavy patient loads.

SUMMARY OF THE PRESENT INVENTION

It is therefore one object of the present invention to generate targets from a memory storage for measuring visual acuity which includes visual targets whose size and orientation are selectively controlled wherein the time required to change from one target to another does not limit the speed with which clinical acuity data can be obtained.

Another object of the invention is to vary the size and relative position of the targets in such a manner that target geometry is the same as moving the target array closer to or further from the patient.

Another object of the invention is to enable the operator to select a black on white or white on black mode of acuity target presentation to the patient which will allow for more adequate testing of low vision patients.

Still another object of this invention is to provide means to selectively display single character or multiple character targets thereby comparing acuity thresholds for "crowded" targets which is significant in the detection of early amblyopes.

A further object of the invention is to randomize the presentation of the targets in such a manner that the patient cannot predict character, orientation, or other critical aspect of the target or targets. Eliminating the possibility of memorization target sequence assures greater validity of the testing.

Another object of the invention is to provide the examiner with the ability to "zoom" target size in either an increasing or decreasing mode in small increments at preselected rates over the entire range of target sizes available along with a digital readout of the size of the target. This feature allows the examiner to secure a target of any size from smaller than threshold vision to full screen size thereby eliminating the restriction to standard sized targets.

A further object of the invention is to provide an instrument including a control console containing pushbutton controls for all features of the instrument, a display for the examiner and a separate display for the patient to view. The examiner controls the instrument from his control console and verifies patient response by viewing his own display.

A still further object is to maintain the luminance and contrast of the patient display in such a way that acuity testing is independent of such factors as ambient testing room illumination. The patient's display unit may be mounted behind a "beam splitter" within a hooded assembly to minimize the effects of ambient illumination and reflections.

An exemplary embodiment includes a control console incorporating the examiner's video display, a patient's video display unit and electronics unit. The control console includes control switches and pushbuttons and digital display of acuity target size. The electronics units include the circuits to generate the composite video signal which produce the acuity targets on the displays.

The exemplary embodiment incorporates the ability to provide within a single video frame a wide range of sizes of acuity targets limited only by the subtence of the minimum number of raster lines needed to make up an acuity target, and the total number of raster lines visible on the patient display itself. Means are provided to display these targets individually or in horizontal groupings, size of the target and display monitor permitting. Access to targets is provided by pushbuttons which elicit fixed size targets typically employed in clinical practice, and a zoom control which causes the targets displayed to grow larger or smaller in minimum size increments governed by the instruments electronics. The rate at which the target size changes is selectable by another control provided. Normal or reverse video presentation is provided as well as an orientation change control and a blank video control.

Other and further objects, uses, features and advantages which are included within the scope of the claims of this invention will become readily apparent to those skilled in the art after reading the following description of a present exemplary embodiment of the invention, given for the purpose of disclosure and taken with the accompanying drawings.

BRIEF DESCRIPTION OF THE DRAWINGS

FIG. 9A is a truth table showing the distribution of raster lines of the target between even and odd fields of the interlaced sweep for each of several target sizes (scale factors), FIG. 15A is a truth table showing the logic relationship of the circuitry in FIG. 15 to implement the change feature.

BRIEF DESCRIPTION OF THE EXEMPLARY EMBODIMENT

Figure 18:
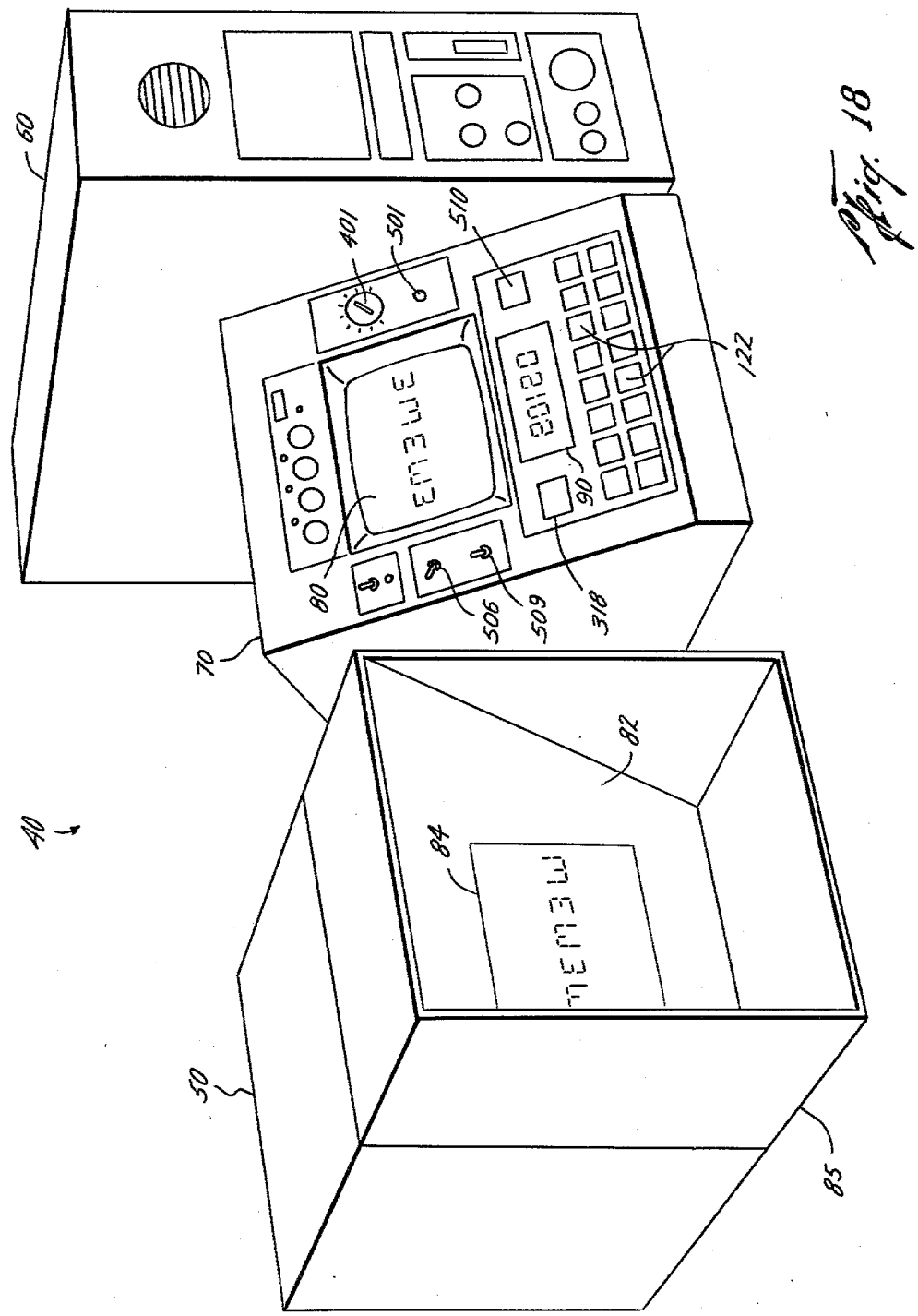
FIG. 18 is a perspective view of one embodiment of the physical components of the present invention, but not shown in their relative operational positions.

Referring now to the drawings, and particularly to FIG. 18, the apparatus of the present invention is generally represented by the reference numeral 10 and generally consists of a patient video display 50 of a size appropriate for a twenty foot patient to display distance, a logic component 60 containing the power supply and circuitry, a control console 70 for the examiner containing a video monitor 80 and controls and switches which will be described hereinafter. The video displays 50 and 70 use a cathode ray tube display although any suitable electro-optical display device including liquid crystal display, matrix display, plasma, gas discharge, and light emitted diodes, and scanning displays, such as generated from a laser light source, may be utilized. While the display 80 may be omitted, it is preferable to have the display adjacent the examiner since the patient display 50 will be spaced from the patient and it is desirable that the examiner and the console 70 be near the patient for ease of communication. While any suitable ophthalmic testing targets may be utilized, the displays 84 and 80 show the use of five "tumbling E" acuity targets, each of which is of equal height to width aspect ratio with letter stroke width and space between strokes equal to one-fifth of the target size. Hence each target in each orientation can be described by a 5×5 matrix of light and dark areas. The patient display 50 includes suitable means for minimizing ambient light and reflections such as a beam splitter 82 of transparent or light absorbing material mounted in front of and at an angle such as 45° to the screen 84 with hooded enclosure 85. However, other ambient light controls may be utilized such as anti-reflection coatings, polarized filters, and light control sheeting. The control of ambient light allows the use of the patient display 50 in rooms of normal levels of illumination thereby allowing the examiner to test acuity under conditions more typical of non-clinical visual environments.

The exemplary embodiment of the apparatus 40 presents target characters singly or in a horizontal line of up to five targets subtending sizes varying over a one to 40 range such as from 20/10 to 20/400 (Snellen notation) in any of four orientations (legs of the E oriented up, down, right or left). The target characters are caused to appear on the video display screens 84 and 80 in either of two ways: First, by pressing any of the pushbutton switches 122 which present targets of fixed Snellen sizes from 20/10 to 20/400; or secondly, by zooming the size of a target character or characters already displayed by actuating a button 501 marked INCREASE/DECREASE in the desired direction. In the latter mode, the available range of targets extends from 20/10 to 20/400. A switch 401 is available to change the rate of zooming as desired. A BLANK switch 510 on the console 70 allows the examiner to remove all targets from the video displays 80 and 84 when the examiner wishes to confer with the patient without distraction. A CHANGE switch 318 changes the orientation of the targets displayed on the screens 80 and 84 without altering their size. In addition, orientation of the displayed targets is changed on a random basis each time one of the fixed size switches 122 is actuated. Switch 509 is available to reverse the video presentation on the screens 80 and 84 providing either the typical black targets on white background or white targets on black background, the latter being advantageous for low vision testing. Switch 506 has a LINE position for displaying five targets or a SINGLE position for displaying a single target thereby allowing the testing of a patient's acuity threshold in a "crowded" versus "uncrowded" fashion. Another feature of the present invention is that the targets remain vertically centered with a constant aspect ratio and proportional character to character spacing as the size of the targets is changed. Also, a visual digital display 90 is provided on the console 70 for indicating the size of the target characters presented on the screens 80 and 84. This feature is particularly useful when utilizing the zoom mode of testing thereby allowing the examiner to conveniently test for acuity measurements at sizes intermediate to those provided by the fixed sizes presented by switches 122.

A typical use with a patient of unknown acuity might be as follows: By actuating switch 506 to the SINGLE position, a single target is presented at a subthreshold level, for example, 20/10 and the examiner zooms the target to an increasing size at an appropriate speed by actuation of switches 401 and 501 until the patient correctly identifies the target orientation. Having arrived rapidly in the vicinity of the patient's threshold, the examiner then presents multiple targets near the level at which the patient correctly identified the first target by actuating switch 506 to the LINE position. Subsequent lines of smaller size are then selected by actuation of the switches 122 until the patient is unable to identify the target orientations adequately to the examiner's criteria. The continuous digital display of the size of the target presented provides a considerable time savings in the examination.

The apparatus 40 will improve the quality of the examination data in several ways. First, by using semi-automated testing, the examiner can standardize his testing procedures, reducing the variability of testing procedure. Secondly, because the apparatus presents targets which are randomly oriented, patient memorization of the acuity targets is precluded, eliminating a significant source of testing error. Thirdly, the beam splitter and hood assembly 50 makes target luminance and contrast (two major testing variables) virtually independent of ambient illumination, allowing testing in the clinic to more closely resemble nonclinical visual environments. Fourthly, the ability to increase and decrease target size by small increments with the zoom control allows for greater resolution of the acuity threshold, yielding data more limited by the patient's acuity performance than by the gross increments in target size imposed by the use of conventional acuity testing devices. In addition, the apparatus 40 provides several capabilities not typically found in most acuity testing devices. The capability of presenting individual targets or a row of targets will allow the examiner to compare acuity thresholds for both of these conditions. The capability of reversing the video presentation will allow for more adequate testing of low vision patients.

Figure 1:
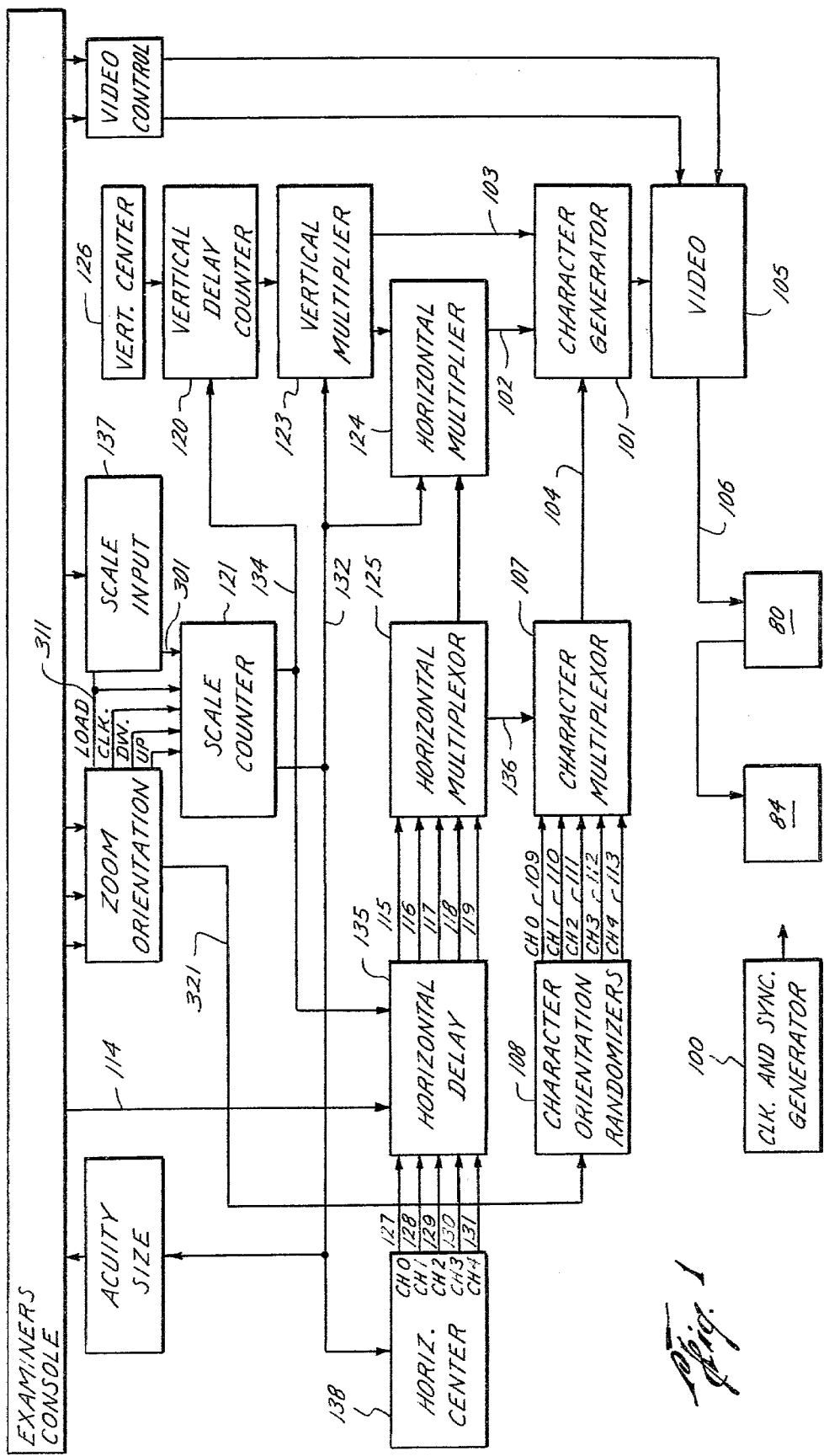
FIG. 1 is a functional block diagram of the system.

Referring now to FIG. 1, the device features the ability to display on one or more video displays 80 and 84, an acuity target character or characters which are stored in a solid state read only memory (ROM) contained in the character generator 101. The character is stored in the ROM in each of four possible orientations (∃,⊔⊔,⊨,⊓⊓). Signals 102 and 103 address the column and row of the character and signal 104 selects the orientation of the character. The selected character is connected to the video mixer and driver 105. Composite video signal 106 is connected to the video displays 80 and 84 (FIG. 18) where the character is displayed.

Character orientation multiplexer 107 produces signal 104 in response to signals such as 109 from orientation randomizer 108 if a single character mode is in use. In the line mode four other signals 110, 111, 112 and 113, are enabled by line signal 114 from switch 506 by way of horizontal delay counter 135, horizontal character multiplexer 125, and line 136.

The horizontal component of size of each of the characters in a line is determined by horizontal delay counter circuits 135 which produce signals 115, 116, 117, 118 and 119. The vertical component of the character size is determined by vertical delay counter 120. Scale counter and multiplier 121 provides signals to delay 120 and horizontal delay counter 135 in response to front panel size selector switches 122 by way of the scale input 137. Scale multiplier 121 also supplies control signals to vertical scale multiplier 123 and horizontal scale multiplier 124 which generate the column 102 and row 103 signals, respectively.

Horizontal character multiplexer 125 multiplexes the horizontal component of the character size signals and supplies them to the horizontal scale multiplier 124.

A novel method is used in the present invention to control the size and position of the characters. The characters are generated and controlled digitally. A single or line of characters is always displayed in the vertical center of the video display. A standard 525 line raster consists of approximately 480 visible lines. Interlaced scan is used in the exemplary embodiment so that two scans of 240 lines are involved. The center of the character therefore is approximately 120 lines from the top of the screen on each of the two scans. Firmware lines to center module 126 furnishes this data to vertical character delay 120. Similarly, read only memories in horizontal counts to center 138 establish the horizontal center of each of the five characters CH0, CH1, CH2, CH3 and CH4 in a line by means of signals 127, 128, 129, 130, 131 to the horizontal delay counter 135.

Signal 132 presets a counter within vertical scale multiplier 123 which determines the number of lines occupied by each of the five vertical segments of the character. The number is dependent upon the scale selected by switches 122.

Signal 134 presets a counter within vertical delay counter 120 after which the video window opens (the top of the character begins) and remains open under control of multiplier 123, that is until the proper number of lines to include each of the segments of the character target have occurred. Similar action occurs with regard to the horizontal size of the character involving multiplexer 125 and horizontal multiplier 124. The action of these circuits is more fully explained below.

Figure 2:
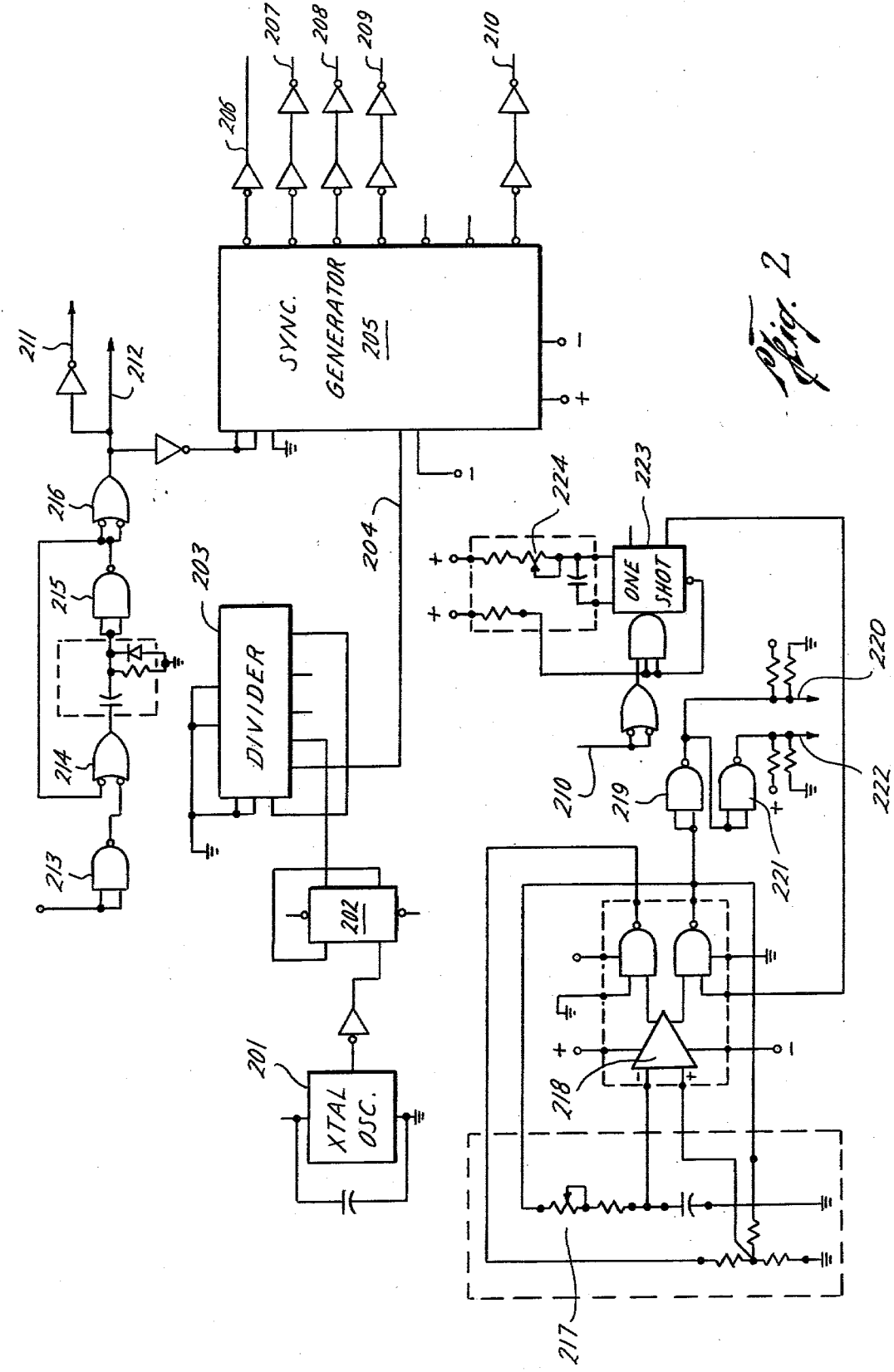
FIG. 2 is a schematic diagram of the clock and sync generator circuits for the system. Also included in this circuit are controls for initial adjustments such as centering and character size calibration. The character size is adjusted to conform to the correct size for the viewing distance. That is, if the distance between patient and video screen is 18 feet for example, the target size is calibrated correspondingly.

Refer now to the remaining figures for a detailed description of the circuits. FIG. 2 is the clock and sync generator which functions under control of crystal oscillator 201. The basic frequency of the oscillator is suitably divided down to reach the standard frequency of 1.26 mhz by dividers 202 and 203. The standard frequency signal 204 excites TV camera and sync generator circuit 205.

Sync generator circuit 205 is a commercially available solid state circuit commonly used to generate the various signals required for video devices such as composite sync 206, horizontal drive 207, vertical drive 208, field index 209 and composite blanking 210. These signals will be found throughout the remaining figures referenced as above.

When power is first applied to the system, signals 211 and 212 initialize the various counters, latches, etc. in the system. Signals 211 and 212 place all the circuits in synchronism. These signals are generated by gates 213 and 216 in a conventional manner. Potentiometer 217, in the feedback path of horizontal clock oscillator comparator 218, is adjusted initially to establish the size of the character appearing on the display to conform to the standard size for the distance from which it will be viewed by the patient. The output of amplifier 218, buffered and inverted by gate 219, is horizontal drive clock signal 220. Signal 222, buffered and inverted by gate 221 is the compliment of signal 220, and is referenced 222 throughout the remaining figures.

Signals 220 and 222 are synchronized by signal 210 and the action of one-shot 223. The length of the output pulse of flip-flop 223 is adjusted by potentiometer 224 and insures centering of the characters in the horizontal plane.

Figure 3:
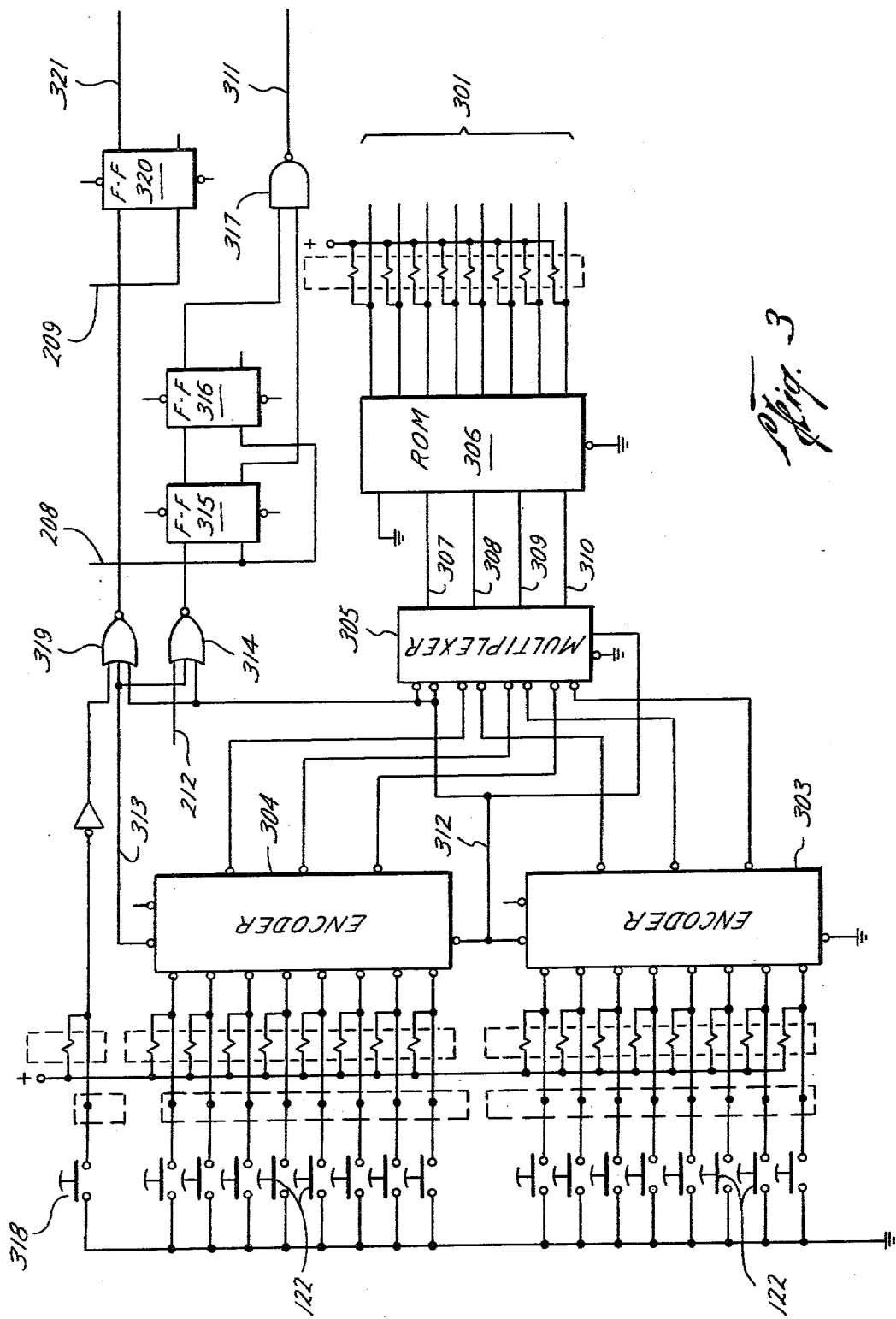
FIG. 3 is the schematic diagram of the size select pushbutton controls used by the examiner and associated scale select logic circuits. Using these controls the examiner can select various preset fixed acuity target sizes and change their orientation on the target displays.

FIG. 3 is the scale select logic circuitry which generates a binary coded signal 301 reflecting the size of the character selected by the front panel switches 122.

Sixteen fixed sizes of acuity target characters are selectable by means of switches 122 in the range 20/10 to 20/400. When one of the switches 122 is pressed a four bit code is generated by encoder circuit 303 or 304 which is multiplexed to ROM 306 through multiplexer circuit 305 and appears on ROM 306, through address lines 307, 308, 309 and 310 in four bit binary format. ROM 306 responds by placing an eight bit code on signal buss 301 corresponding to the scale (size of the target) selected. This code is loaded into scale size counters 601 and 602 in FIG. 6 by signal 311.

Signal 311 is produced by either signal 212 or 313, depending upon which button was pushed, through gate 314, de-bounce flip-flops 315 and 316 and gate 317. Signal 311 is synchronized by signal 208.

Gate 319 responds to signals from change orientation button 318 and signals 212 and 313 so that a change in orientation always occurs as different character sizes are selected or when button 318 is pushed.

Flip-flop 320 de-bounces the signal from switch 318 and generates the change orientation signal 321. The signal is synchronized by signal 209.

The automatic change of character orientation when character size is changed and the ability of the clinician to change character orientation at will, together with the random change which occurs, is a novel feature of the invention.

Another novel feature of the invention is the zoom capability of the device and the availability of various rates of change in size in either the increasing or decreasing size zoom mode.

Figure 4:
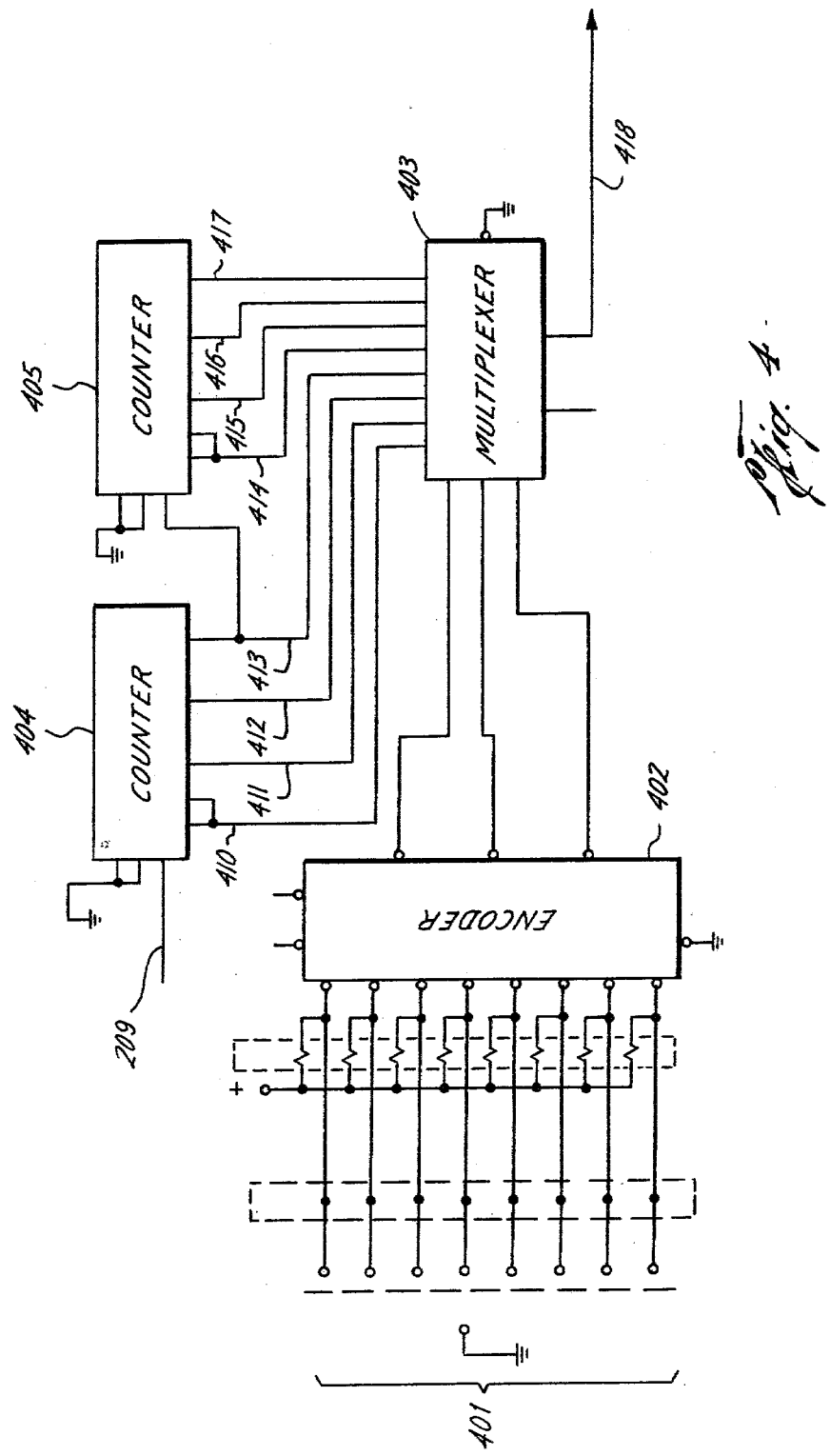
FIG. 4 is the schematic diagram of the circuitry associated with the rate of speed aspect of the novel zoom feature of the invention. The examiner selects the speed with which the character size increases or decreases in zoom mode by means of this control and circuitry.

FIG. 4 illustrates part of the circuitry involved in the zoom mode feature. The zoom feature is implemented by simply adding to (or subtracting from) the selected character size established by signal 301 stored in counters 601 and 602, FIG. 6. The rate of change in size is selectable by rotary switch 401, FIGS. 4 and 18. A one of eight code generated by the position of switch 401 is converted to a three bit code which addresses an input to multiplexer circuit 403.

Signal 209, as a matter of convenience, is the source of the scale change clock signal 418. Ripple counters 404 and 405 divide signal 209 into eight different signal rates. Each of the signals 410-417 serve as an input to multiplexer 403.

The three bit address signal connected to multiplexer 403 selects one of the inputs so that output signal 418 is a scale change clock signal selected by switch 401. Signal 418 is utilized by circuits shown in FIG. 6 and is described in that section.

Figure 5:
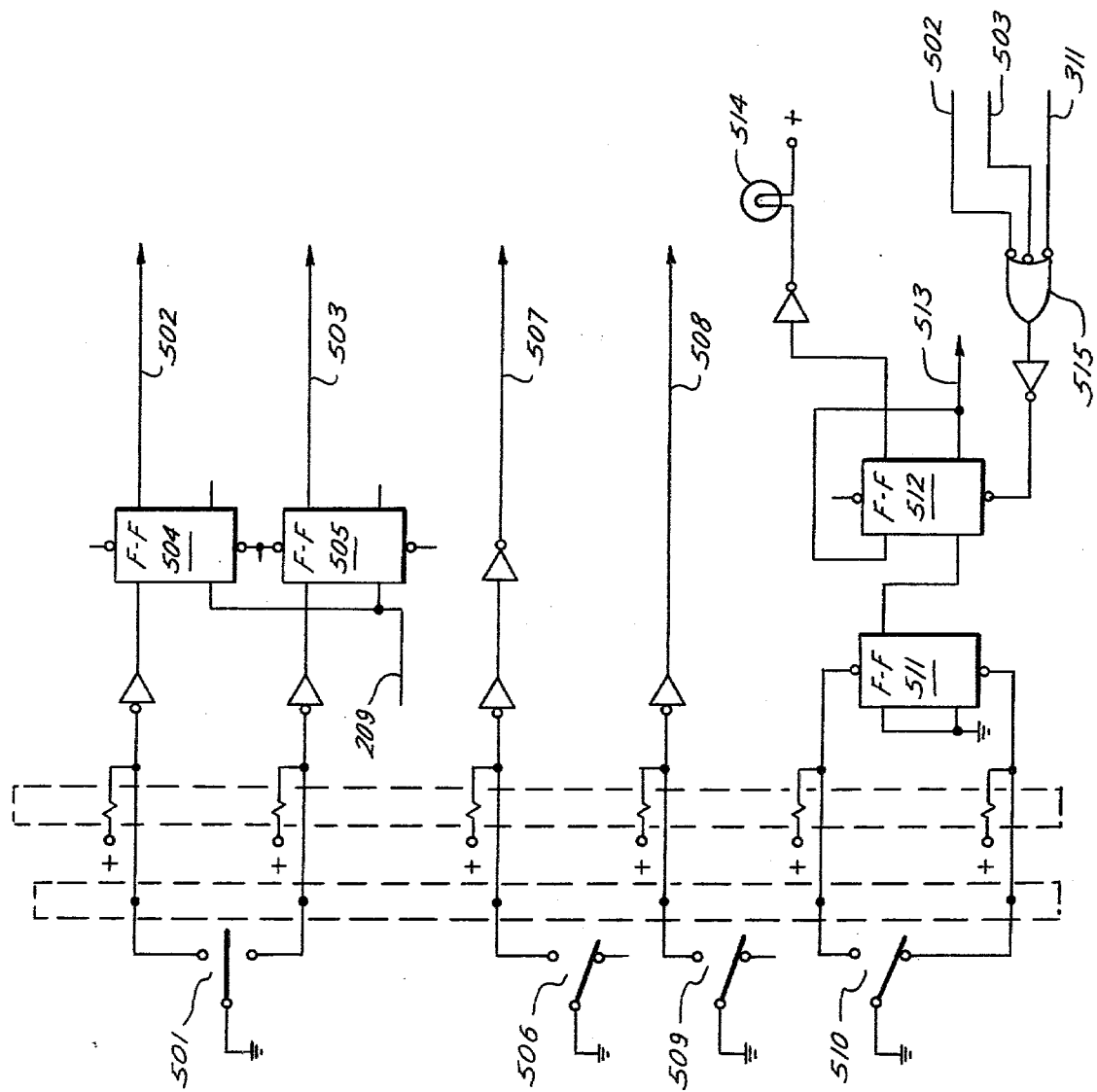
FIG. 5 illustrates the remaining controls available to the examiner. Through the use of controls shown on this schematic he can steadily increase (or decrease) target size in the zoom mode; select a single character target or multiple character line of targets; change the video presentation such as from black on white to white on black; or blank the screen.

Referring now to FIG. 5, certain other front panel switches and features of the invention are illustrated. Switch 501 allows the selection of either increasing size or decreasing size in zoom mode. Signal 502 enables the increasing size. Signal 503 enables decreasing size. Flip-flops 504 and 505 de-bounce the switch 501 signal. Signal 209 synchronizes the signals.

Switch 506 enables the operator to select either a single character display or a line of five characters. Signal 507 enables the proper circuits shown in FIG. 14.

Signal 508 enables normal or reverse video presentation as selected by switch 509. Normal is defined as white target on black screen. Signal 508 is associated with circuitry shown in FIG. 12.

During the course of a typical examination the clinician may wish to blank the video screen for a time and consult with his patient. Switch 510 generates a signal, de-bounced by flip-flops 511 and 512 to implement the feature. This signal 513 is associated with circuitry shown in FIG. 11.

While the system is in the blanking mode, lamp 514 is lighted. The examiner may continue the examination where he left off by pressing switch 510 thus removing the blanking and displaying the same characters or he may elect to go immediately into zoom mode. By pressing switch 501 either signal 502 or 503 operate gate 515 and flip-flop 512 thus removing the blanking and presenting characters of changing size on the screen.

The clinician also has the option of restoring the characters on the screen in a different size. In this case, the selection of a new size by operating one of the switches 122, produces signal 311 which also removes the blanking.

Figure 6:
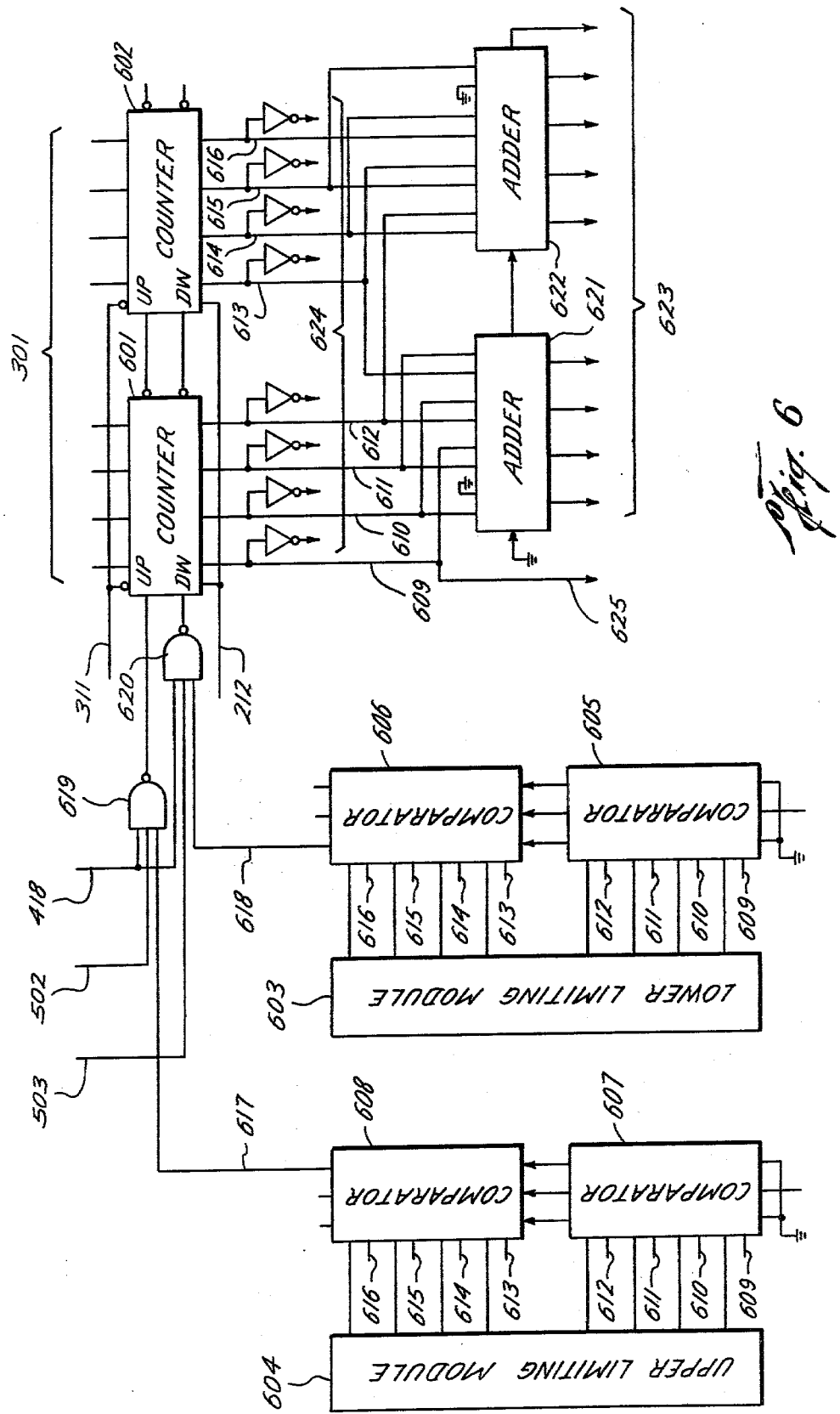
FIG. 6 is a schematic diagram of the scale multiplier circuits which generate the character sizes selected by the front panel switches shown in FIG. 3. Firmware limits for the smallest and largest characters available are included in the circuitry.

Referring next to FIG. 6, it is apparent that many of the signals described in the preceding descriptions appear. Before examining the use of these signals certain firmware considerations should be explored.

Character size must be limited, particularly in zoom mode both in terms of minimum and maximum size to assure that a target is made up of a minimum number of raster lines and that an appropriate border is left between the top and bottom of the visible video field. The minimum character size has been determined to be made up of five raster lines for a character five segments in height. From a practical viewpoint the maximum size is determined to be 400 raster lines. Firmware limiting modules 603 and 604 establish these limits in the device being described.

An eight bit code from lower limit device 603 is supplied to cascaded comparator circuits 605 and 606. Similarly the coded upper limit is applied to comparators 607 and 608.

Recalling that counters 601 and 602 contain coded scale data from switches 122 via counter preset input signals 301, it is apparent that a comparison between the outputs of counters 601 and 602 will confirm that the selected scale falls between the lower and upper limits established by modules 603 and 604. Counter output signals 609-616 therefore are connected to the comparators 605-608. If the contents of counters 601 and 602 fall between the limits established by modules 603 and 604, signals 617 and 618 partially enable gates 619 and 620, respectively.

In the zoom mode assume that signal 503 is present, that is, the decreasing size presentation is in progress. Signal 503 completes the enabling requirements of gate 620 and each clock signal 418 is subtracted from the contents of counters 601 and 602. Similarly, if we assumed that we were operating in the zoom increasing size mode, signal 502 enables gate 619 so that signal 418 pulses are added to the contents of the counter.

In either mode, when a limit is reached, either signal 617 or 618 is removed and changes in counter content ceases. The size of the displayed character remains fixed at this point.

The actual size of the character is defined in terms of the number of raster lines of which it is made. If counters 601 and 602 contain data requiring a character size scale factor of two for example, a total of 2×5 lines will be required to display the character. Since interlaced sweep is involved the total number of lines must be divided by two. In this case, each field will provide five of the total raster lines required to generate the character.

Adder circuits 621 and 622 are wired to multiply scale factor signals 609-616 by a factor of 2.5 so that signals 623, which are the outputs of the adders, will contain data indicating the number of lines from the start of the video window to the center of the character. For our exemplary scale of two signals 623 would therefore be 2×2.5 or five raster lines. Signal 623 is utilized in FIGS. 7, 8 and 14.

With respect to the horizontal size of the characters, signal 623 is used to control the number of counts to the center of a character. Number of counts is analogous to number of raster lines.

The scale factor signals 609-616 are buffered and inverted and are referenced 624 in FIG. 6. Signals 624 are utilized in FIGS. 9 and 13. Signal 625, which is the least significant bit of the scale factor word, is used in FIG. 9.

Figure 7:
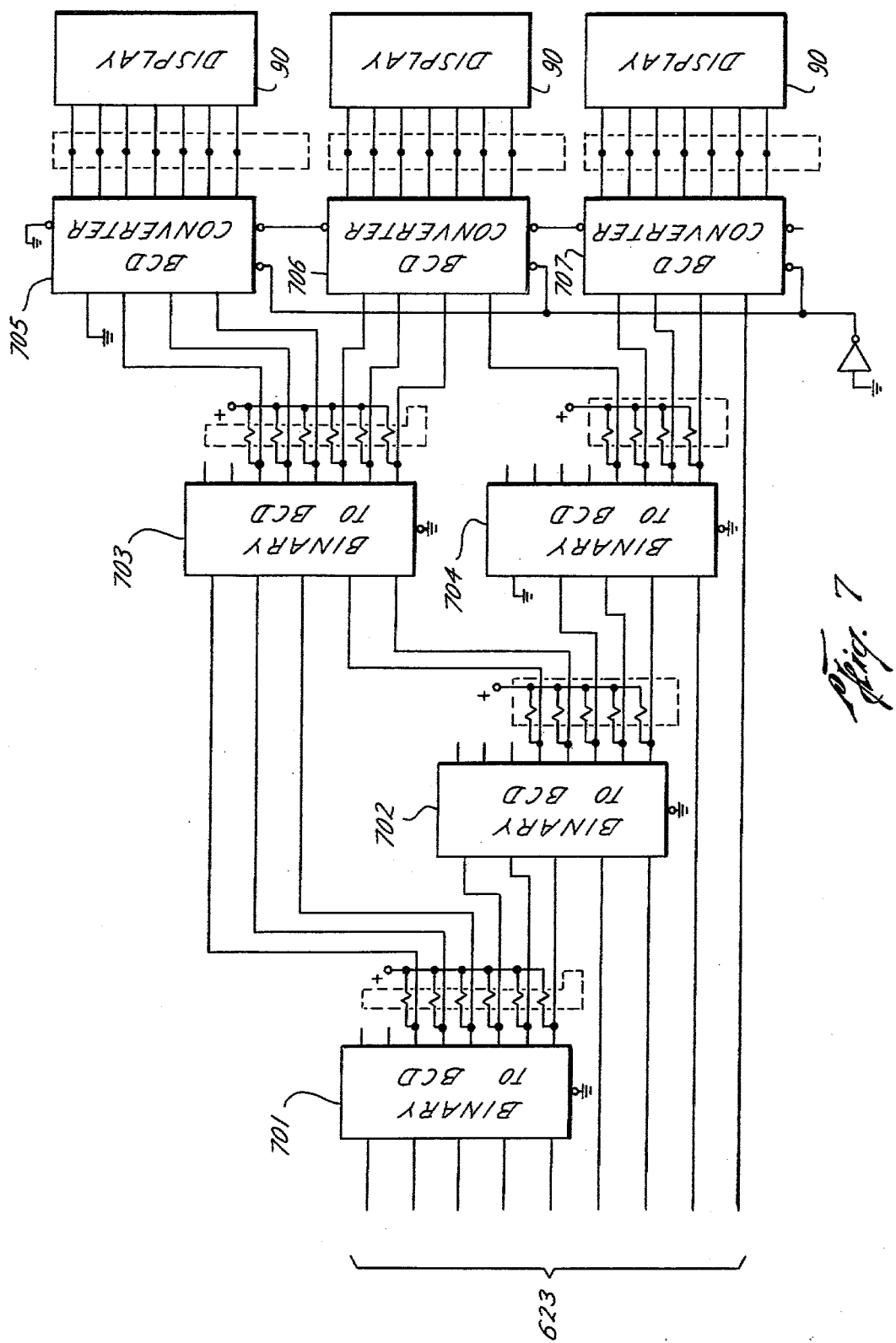
FIG. 7 is a schematic diagram of another feature of the invention. The size of the character is displayed digitally by this circuitry. The feature is particularly useful in zoom mode where character sizes are available to the examiner between the preset fixed target sizes.

Referring next to FIG. 7, we find illustrated conventional digital display and driver circuits. Although the circuitry is conventional the feature it provides is novel. Signals 623 are decoded by binary to BCD modules 701, 702, 703, and 704 and in turn by BCD to seven segment converters 705, 706 and 707 to drive display 90 which reflect the denominator of the acuity target or character size. For example, the illustrated display 90 may show the figure "120." The character size is then "20/120" with the "20" being hardwired into display 90 (FIG. 18).

In the zoom mode the examiner may wish to begin his test with characters of a size smaller than his patient can distinguish. While increasing target size with the zoom control, the display 90 continually shows actual target size accurately. When the patient signals that he can distinguish a character, the zoom is stopped and the target size may be recorded. Quantitative information is therefore obtained that heretofore has been unavailable due to the limitations of standard or fixed size character displays.

Figure 8:
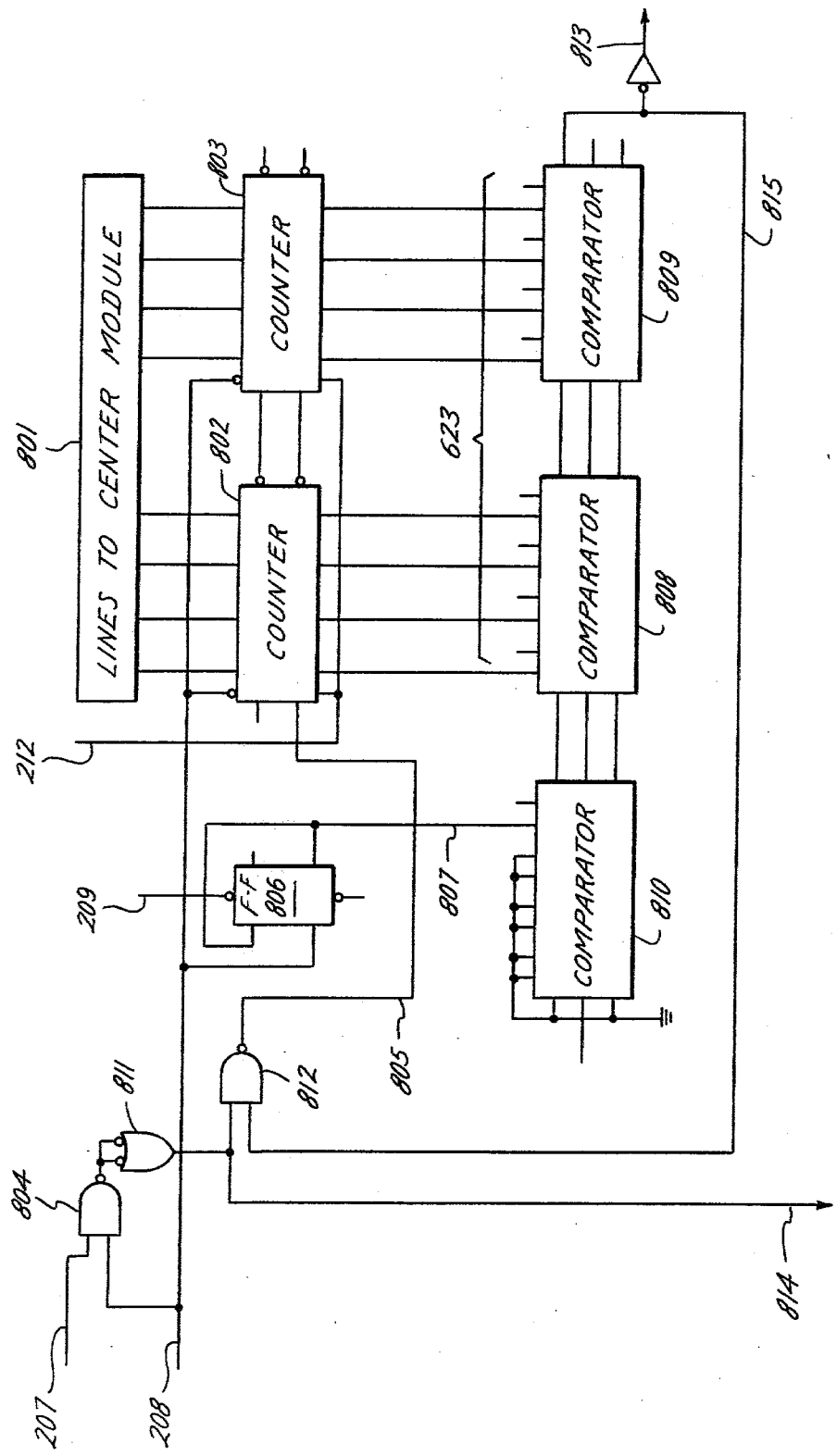
FIG. 8 is a schematic diagram for the vertical delay counter circuits which control the vertical component of the character size.

FIG. 8 illustrates the vertical delay counter circuits which function to establish the top edge of the characters displayed. Firmware module 801 contains the number of raster lines per field from the top to the center of the display screen. Module 801 is connected to the preset inputs of counters 802 and 803. When the vertical drive pulse 208 occurs, the contents of 801 is loaded into the counters. The counters are designed to count down from this value toward zero.

Flip-flop 806 is set by signal 209 which synchronizes the circuit action to coincide with an even field. Signal 807 identifies the odd field in the interfaced vertical scan. When flip-flop 806 is set by signal 209, it is toggled by signal 208. On the next occurrence of signal 208 the scan will be in even frame and signal 209 will not occur. Signal 208 then toggles flip-flop 806 to the set condition to produce signal 807.

One input to comparator circuits 808 and 809 is signal 623 which is the number of lines for half of the character height. This number is a function of the selected scale as previously discussed.

Gates 804, 811 and 812 pass signal 207 to counters 802 and 803. The counters count signal 207 pulses, subtracting from the count loaded into them by 801. The counting continues until the 802, 803 number is equal to the signal 623 number to which it is being compared by circuits 808 and 809. When equality between the two numbers is detected signal 813 is produced which opens the vertical window and the top edge of the character begins. The count at which equality will occur is adjusted one count by signal 807 which injects one count into comparator 810. This count is added to the count contained in signal 623 and makes the count compatible with interlaced scan requirements.

Figure 9:
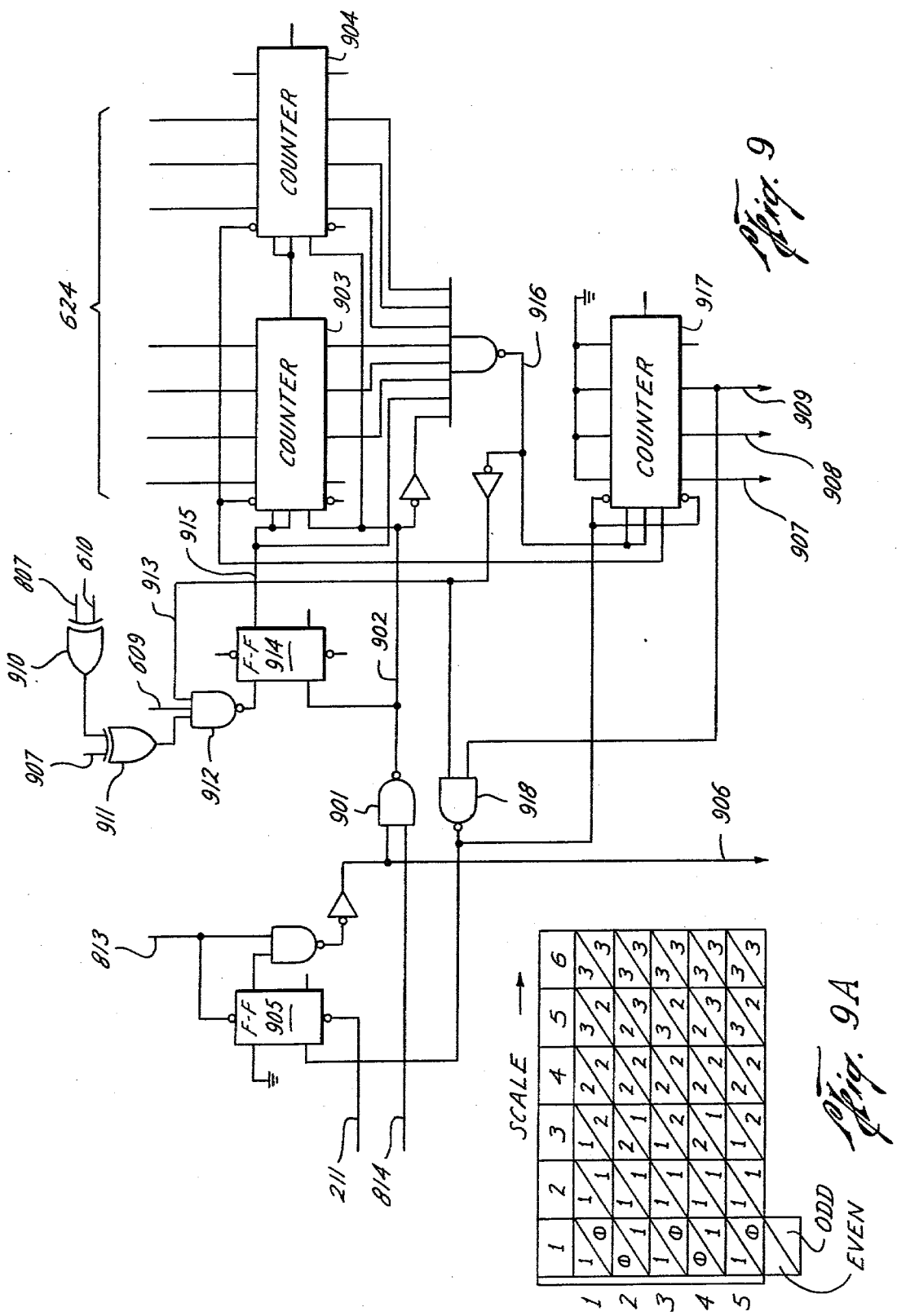
FIG. 9 is a schematic diagram of the vertical scale multiplier circuits.

Signal 814, which is used in FIG. 9, is produced by gate 811.

As the vertical scan continues, counters 802 and 803 are inhibited from counting by signal 815, which inhibits gate 812. The vertical window remains open under the control of the circuitry in FIG. 9.

Referring now to FIG. 9, signal 814 has been inhibited by gate 901. When the vertical window signal 813 sets flip-flop 905, which enables gate 901, signal 902 is used to clock counters 903 and 904. When flip-flop 905 is set and signal 813 is present, a vertical window open signal 906 is produced.

Figure 12:
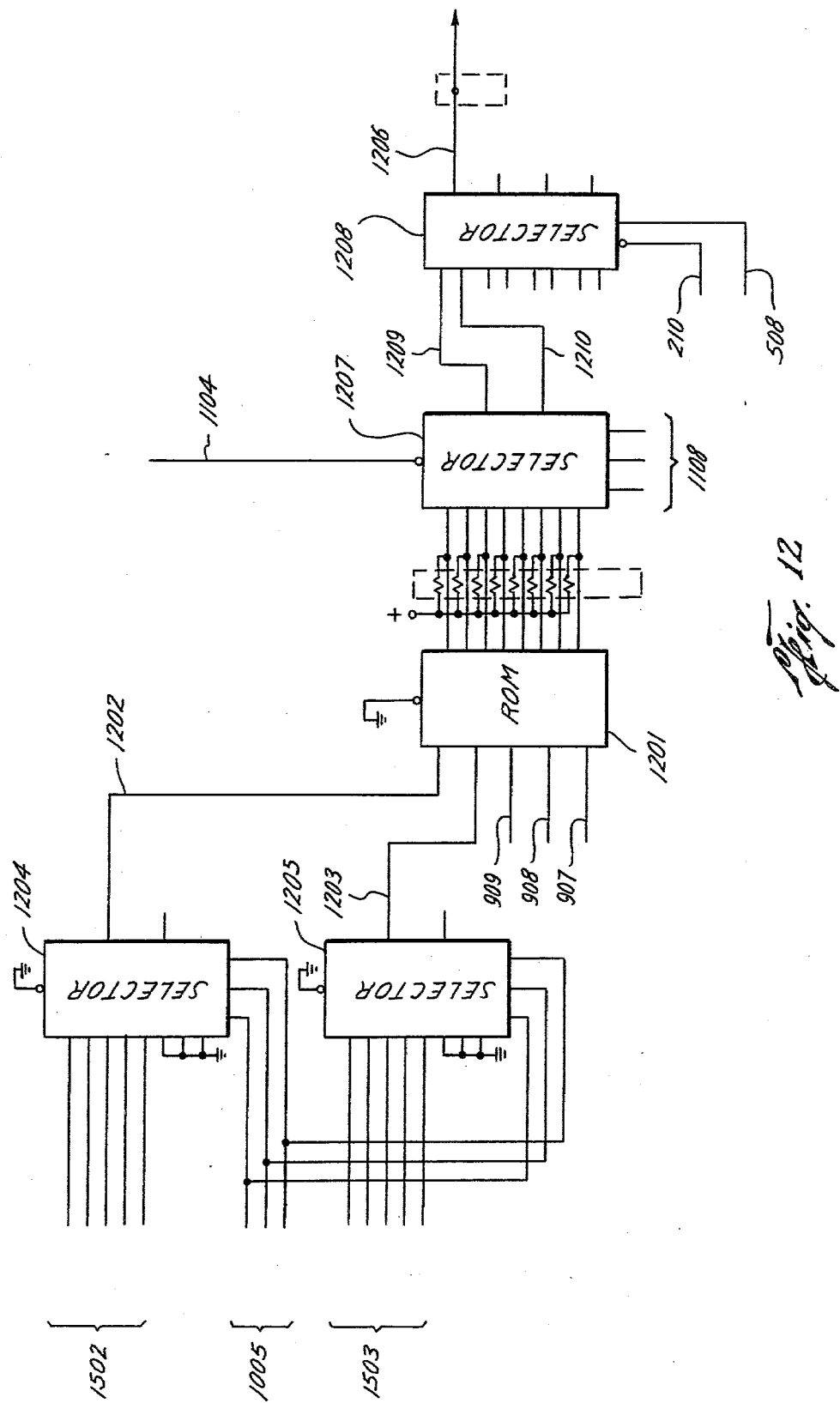
FIG. 12 is the video multiplexer circuits which combine the various signals into video pulses.

The primary function of the circuitry in FIG. 9 is to select the row address of the ROM 1201, FIG. 12, where the acuity target characters are stored. As the row addresses are sequentially selected, the vertical window is held open for a number of lines compatible with the selected scale. Signal 624 contains the scale data.

For example, if the character size is 20/5, scale = 1, the data in 624 is one line. Therefore, each of the five vertical segments of the character will be made up of one line, making a character of five lines high. Due to the interlaced scan, a portion of the five lines will occur within the even field and the remainder will occur within the odd field. The required relationship is shown in FIG. 9A. Assuming the character to be an ordinary "tumbling E", FIG. 9A illustrates the relationship between odd and/or even numbered scale sizes and the odd or even fields of the interlaced sweep for scale factors up to six.

From the table it can be seen that for a scale factor of one, three lines occur in the even field and two occur within the odd. A scale of three consists of a total of 15 lines; seven occurring in the even and eight in the odd frame, etc.

Exclusive OR gates 910 and 911 and NAND gate 912 are driven by signals 907, 807, 610, 609 and 913 and supply data to flip-flop 914. Flip-flop 914 functions to inhibit counters 903 and 904 counting for one count.

Counters 903 and 904 are counting signal 902 pulses. If 914 is set by the combined action of the output of gate 912 and signal 902 then signal 915 is low and the next signal 902 pulse would clear 914 and 915 would be high. The counters 903 and 904 would be inhibited due to the low signal prior to the 902 pulse and therefore ignore one 902 pulse. One vertical segment would therefore have one less count than other segments. If the scale factor is an even number, all vertical segments have equal number of lines. If the scale factor is an odd number, a difference of one line count between successive segments is required.

Counters 903 and 904 count toward zero from the numbers loaded into them by signals 624. When the count reaches one, signal 916 clocks counter 917 which addresses the next segment in ROM 1201. Signal 916 also reloads the scale factor number into counters 903 and 904 and the counting begins again for the vertical segment just addressed. The inhibiting of counters 903 and 904 for one 902 pulse allows one additional 902 pulse to occur before signal 916 is produced.

When the counting sequence for the last vertical segment of the character is completed, signals 913 and 909 cause the output of gate 918 to reset flip-flop 905 and the vertical window is closed.

Figure 10:
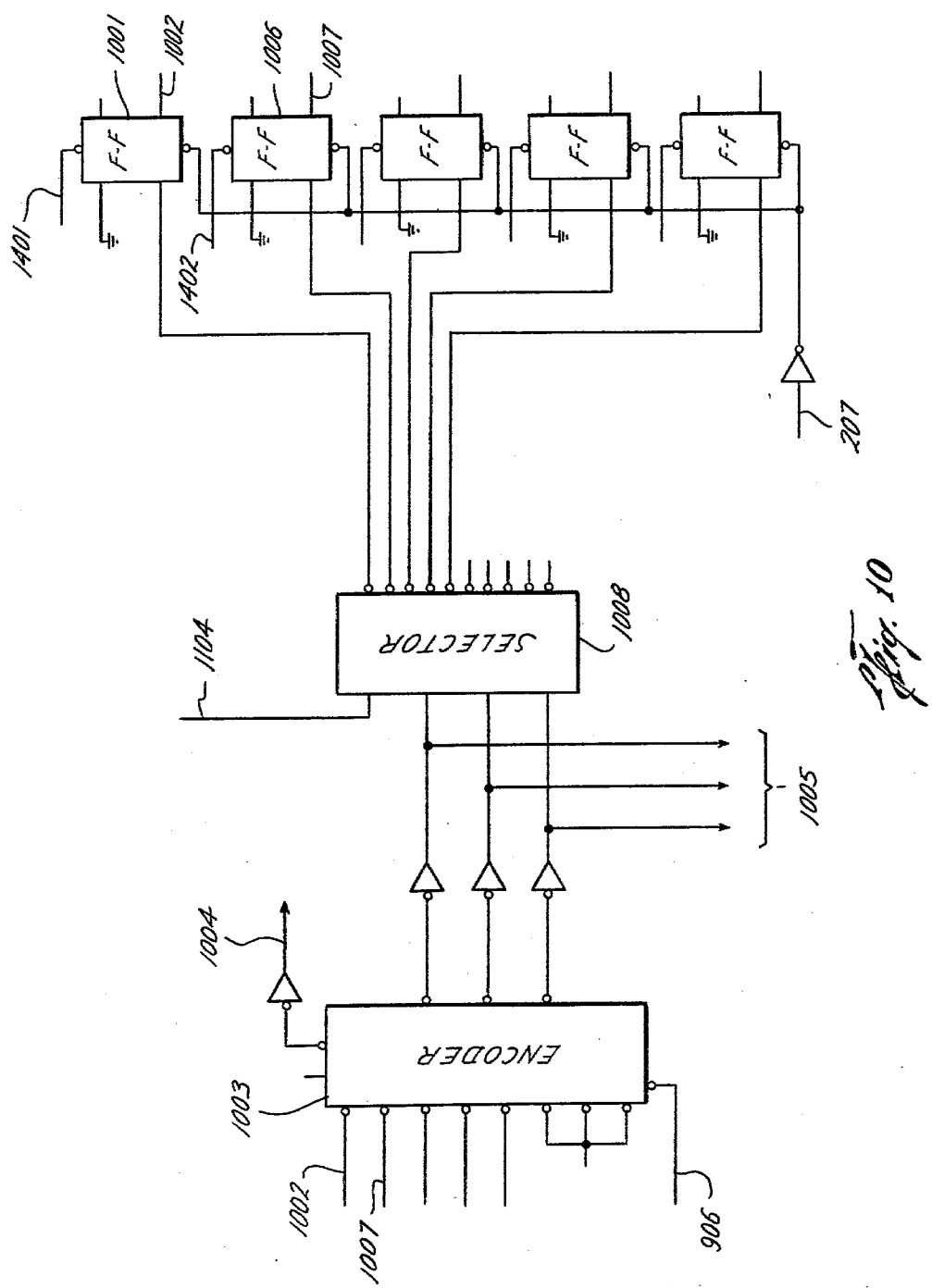
FIG. 10 is a schematic diagram of the horizontal character multiplexer which controls the position of the characters when multiple characters are presented on a horizontal line (line mode)
Figure 14:
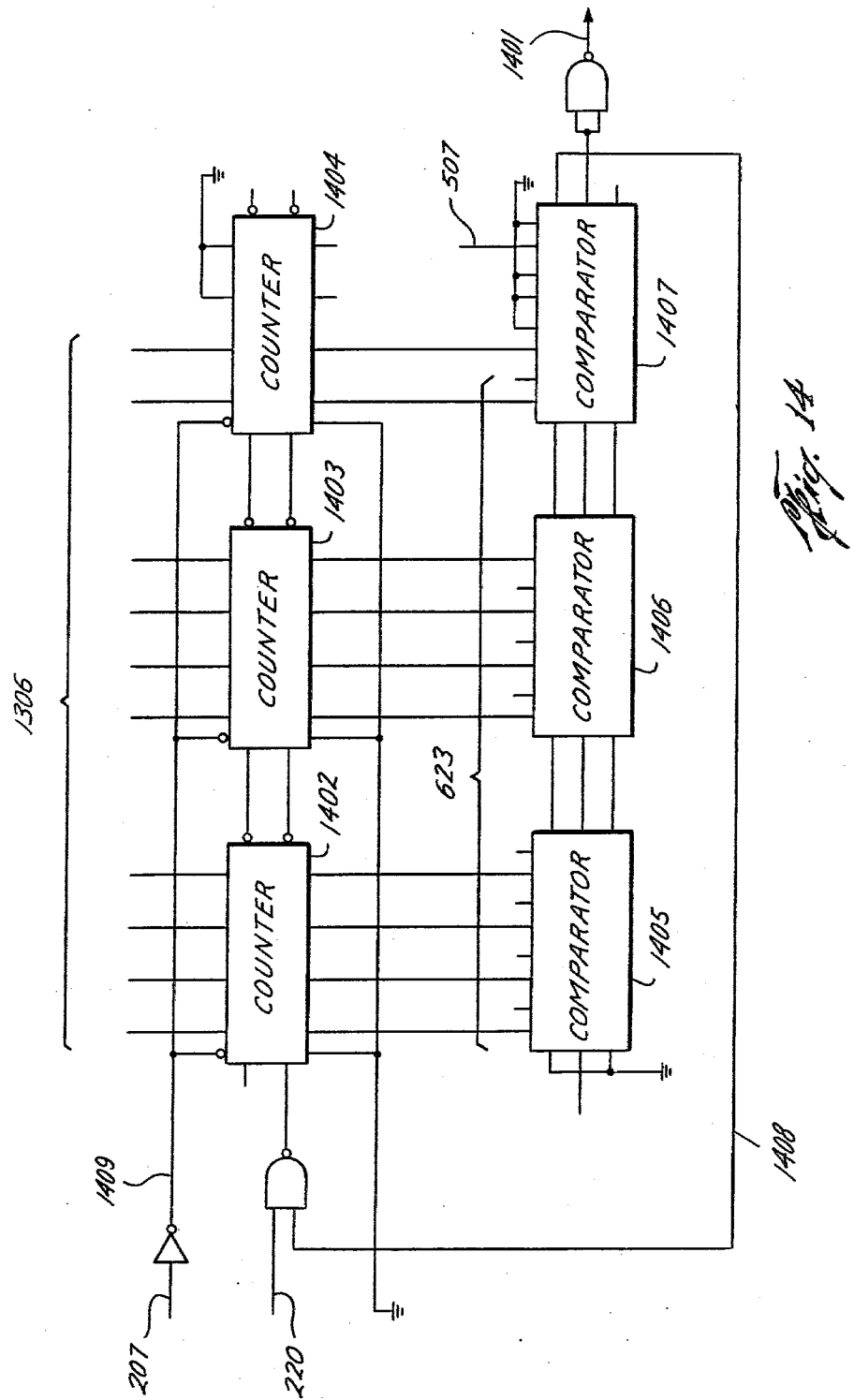
FIG. 14 is a schematic typical of the five horizontal delay counters in the system, one for each character in a line mode presentation.

FIG. 10 shows the circuitry to multiplex signals from the horizontal window counters for each of the five characters in a line presentation. Signal 207 initiates the action of this circuitry. A horizontal window counter is shown in FIG. 14. The counters count from the left edge of the screen to the center of each character. The count is dependent upon which of the five characters is involved and upon scale or character size. The count to the center of the center character is of course the same regardless of scale. The operation of the counters is explained more fully later, however, an output signal such as 1401 from character zero (the left most character) counter sets flip-flop 1001 producing signal 1002. Priority encoder 1003, enabled by the vertical window open signal 906, generates signal 1004 which opens the horizontal window in response to signal 1002. The output of 1003 produces signals 1005 which is used to select the orientation of the character in ROM 1201.

The horizontal window having been opened for character zero remains open under the control of other circuitry to be described. At the end of the character, signal 1104 resets flip-flop 1001 via selector circuit 1008 and closes the window. Subsequently a signal such as 1402 sets flip-flop 1006 producing signal 1007 and the window is opened for character one in the same manner as before. Signal 1005 routes signal 1104 to reset 1006 through selector circuit 1008.

In summary the circuitry in FIG. 10 multiplexes signals from horizontal window counters to open and close the horizontal window for each of the five characters during the vertical window open signal 906 and is synchronized by the horizontal drive signal 207.

Figure 11:
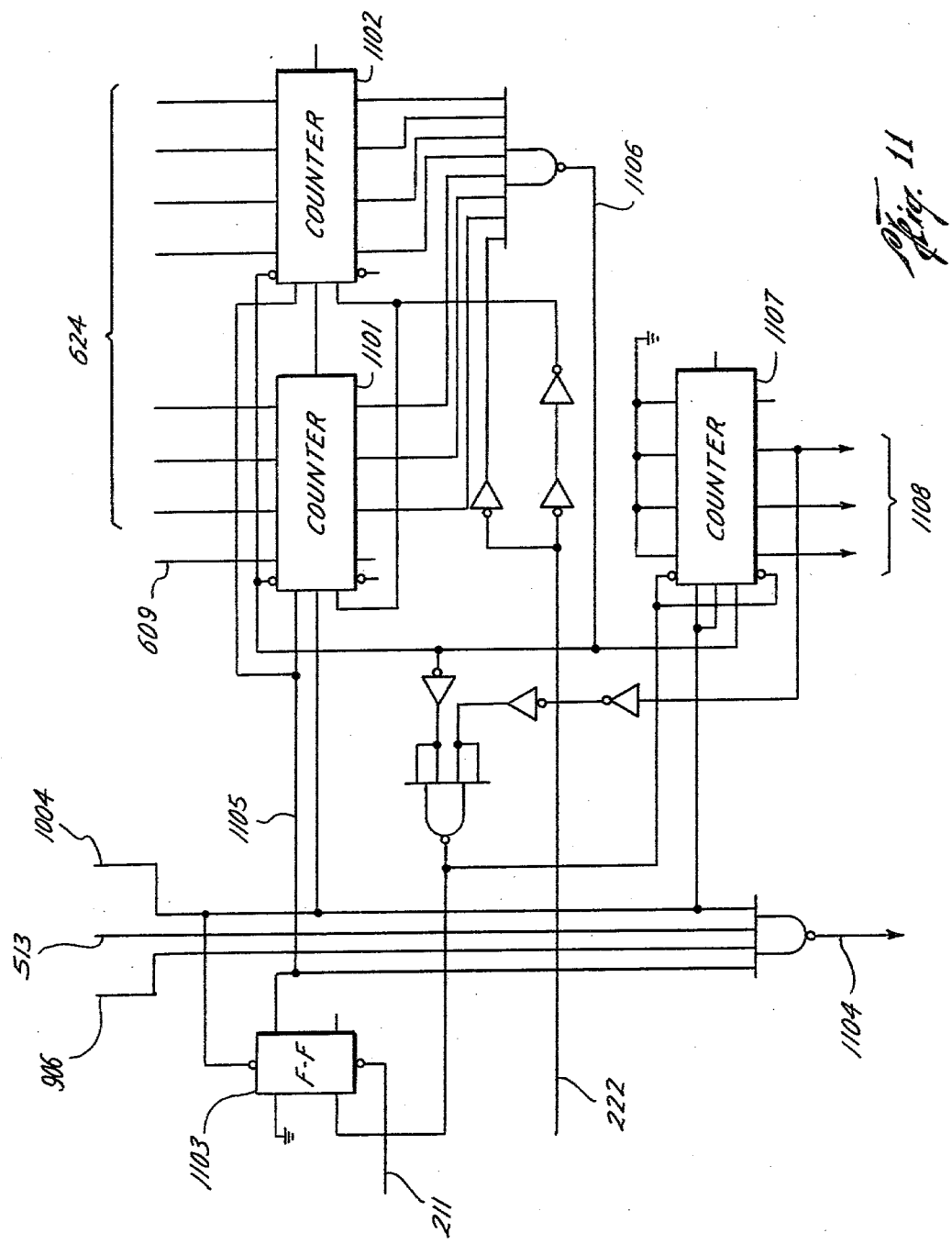
FIG. 11 is the horizontal scale multiplier circuitry.

FIG. 11 is the horizontal scale multiplier circuit which serves the same function in the horizontal realm as the circuitry in FIG. 9 does in the vertical realm. Signals 609 and 624 contain the scale information which is loaded into counters 1101 and 1102. Signal 1004 sets flip-flop 1103. Signal 1105 enables the counters which count signal 222 pulses from the value preset into them by signals 624 and 609 toward one. When a value of one is reached signal 1106 increments counter 1107 one count changing signals 1108 to address the next segment of the character in ROM 1201 and reloading counters 1101 and 1102 with signal 624 and 609 respectively. At the end of the fifth segment, signal 1106 resets flip-flop 1103 closing the horizontal window for the first character. When the next 1004 signal occurs the action repeats. Signal 1104 occurs in response to 906, 513 and 1004 to control the window as previously described.

Figure 15:
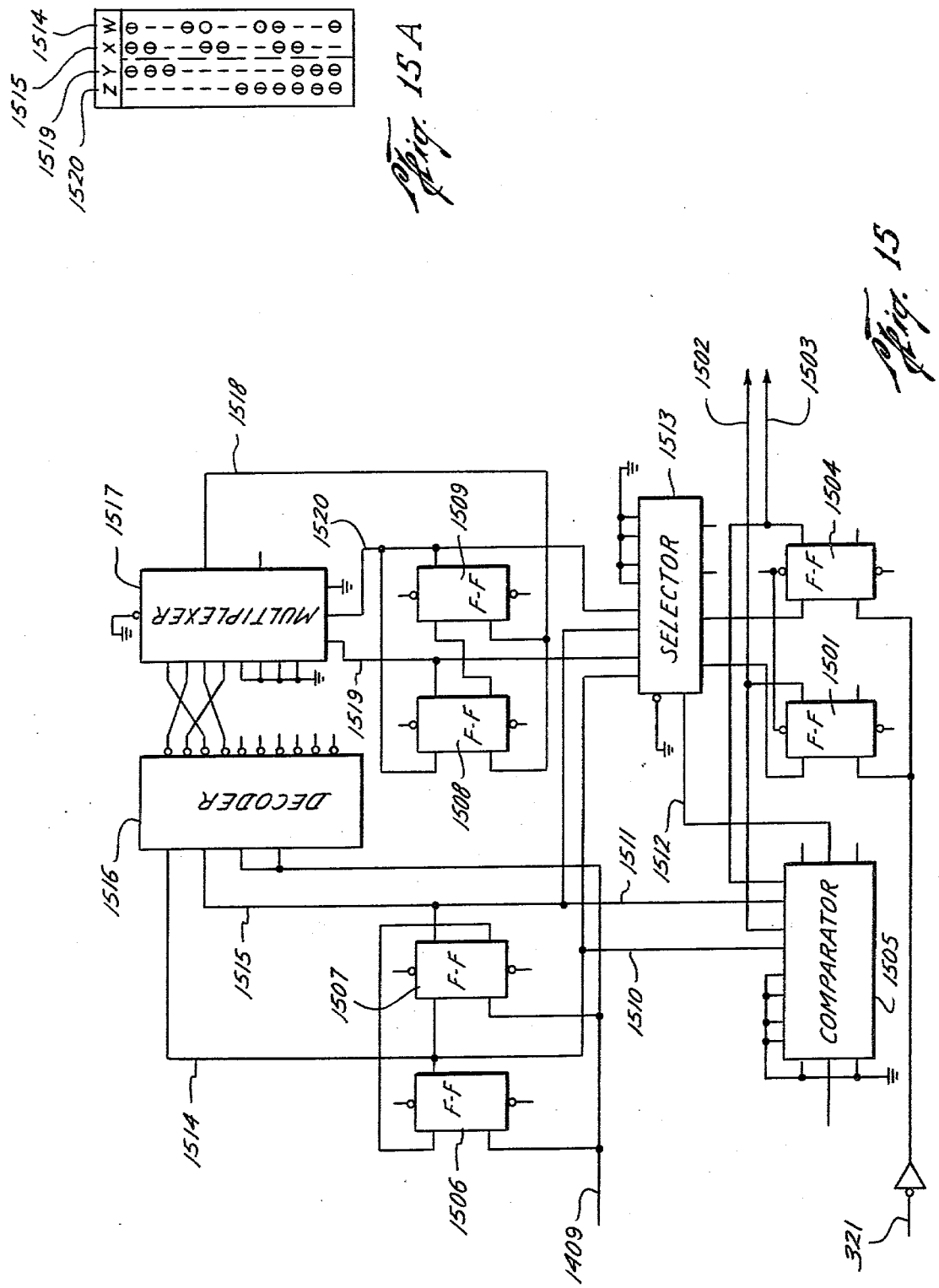
FIG. 15 is the character orientation randomizing circuitry. This circuitry responds to signals from the change orientation button associated with FIG. 3. A novel feature is the ability of the circuitry to recognize the orientation of the acuity character prior to receipt of the change signal. In responding to the change signal the random selection of orientation is limited to orientations other than the one existing prior to the change signal. A change in orientation is thus assured each time the button is pressed.

FIG. 12 illustrates the video multiplexer circuitry. The acuity target characters are stored in ROM 1201 in several different orientations. Signals 907, 908 and 909 together with signals 1108 select the row and column of the stored characters. Signals 1202 and 1203 determine the orientation of the character selected by completing the addressing requirements of ROM 1201. Signals 1202 and 1203 are developed by data selector circuits 1204 and 1205 which respond to signals such as 1502 and 1503. The latter signals come from character orientation randomizer circuits for each of the five characters. These circuits, one of which is shown in FIG. 15 are to be described. Data selector 1204 selects one orientation signal from the 1502 group while data selector 1205 selects from signals 1503. Each character in the line of five is separately selected by the character select signals 1005.

The video output signal 1206 is enabled by signal 1104 through data selector 1207. Blanking control is by signal 210 and normal or reverse video control is by signal 508. 1208 is a data selector circuit which is controlled by 508 to select either signal 1209 or its complement 1210 to reverse the video presentation.

Figure 13:
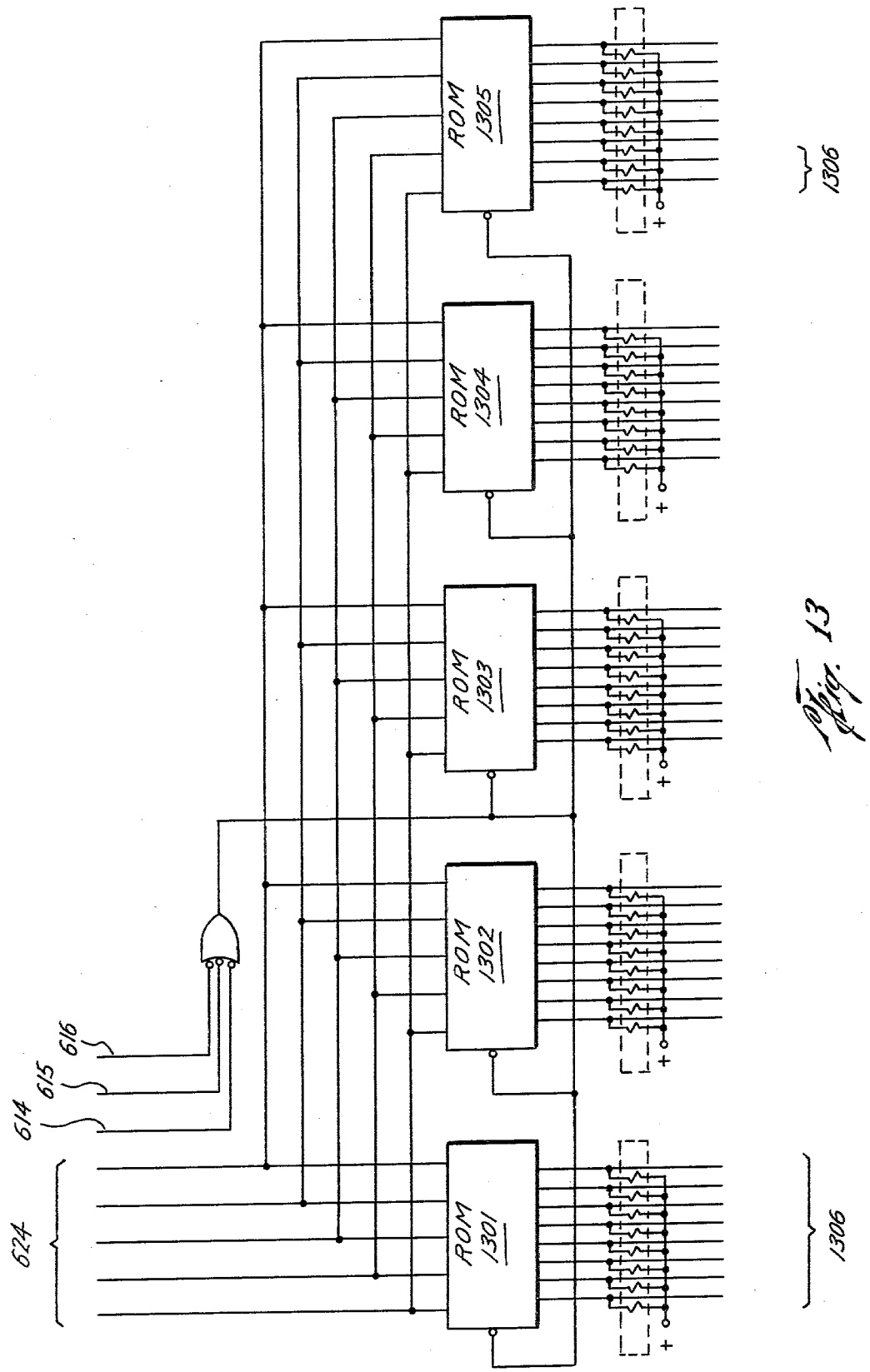
FIG. 13 is the schematic of the horizontal center select circuits that contain the information which controls the horizontal position of each character in line mode for the various character sizes.

FIG. 13 is a circuit containing five ROM memory devices 1301, 1302, 1303, 1304 and 1305. The ROMs contain the horizontal counts to center data for target characters zero, one, three and four in the line mode. The counts to center data for character two is fixed since it does not change with scale. A variable count to character center is required for the other characters as scale is changed.

On the lowest scale, the line of five characters are spaced apart a distance equal to one character. As scale increases the outside most characters move outwardly toward the edges of the video displays 84 and 80 to maintain the one character spacing. The ROMs therefore contain a count to center at each scale for each character. A 10 bit code is required so that ROM 1305 contains the two most significant bits of the data for each character, ROM 1301 contains data for character zero and 1302, 1303 and 1304 contain data for characters one, three and four, respectively.

The output signals from the ROMs, for example 1306 from ROM 1305, are connected to individual horizontal delay counters for each character.

As the scale increases, the outside characters are eliminated from the display by signals 614, 615 and 616 before they approach the edge of the screen. Characters zero and four are eliminated first. Increasing the scale further, results in the elimination of characters one and three leaving character two which can be expanded to 20/400 scale. At this scale the character occupies the entire display screen. Signals 624 and 614, 615, 616 supply the scale data to the ROMs which respond by furnishing the counts to center data to each of the individual horizontal delay counters.

FIG. 14 shows a typical horizontal delay counter for one character. The counts to center data signals 1306 are loaded into counters 1402, 1403 and 1404 by horizontal drive pulse 207.

Comparator circuits 1405, 1406 and 1407 compare the contents of the counters with data signals 623. Signals 623 contain the count from center to character edge or half of the character width count. Counters 1402–1404 count clock pulses 220 downward toward zero. When the count is decreased to be equal to signal 623, the comparators produce signal 1401 which opens the horizontal window and the edge of the character appears on the video display. The action of signal 1401 was previously described under FIG. 10. As the counter counts the next count after equality between 623 and counter contents, a signal 1408 inhibits counting by stopping clock pulse input to the counters.

FIG. 15 shows the circuitry used to randomly address a character in ROM to achieve the random orientation feature. The circuit is typical of five in the system, one for each character in the line. The result of the two bit random address code 1502, 1503 was described in conjunction with FIG. 12. Obviously, the two bit code allows selection of four different orientations. To insure that a change in orientation always occurs when requested by signal 321, the circuit is designed to prohibit the current or present orientation of a character. One of the three remaining orientations will occur in response to 321.

The current orientation code 1502 and 1503 is contained in flip-flops 1501 and 1504 and serves as an input to comparator circuit 1505.

Signal 321 clocks the flip-flops to store a new orientation code. The code loaded may come from either of two sources, flip-flops 1506–1507 or 1508–1509. The outputs of 1506 and 1507 are signals 1510 and 1511, respectively, which are also connected to comparator 1505. If the two sets of coded signals 1502–1503 and 1510–1511 are identical, comparator 1505 output signal 1512 selects the outputs of flip-flops 1508 and 1509 through data selector 1513. If the two coded signals are not equal, data selector 1513 loads the outputs of flip-flops 1506–1507 into flip-flops 1501 and 1504.

Signal 1409 is the horizontal drive pulse and clocks flip-flops 1506 and 1507 which are connected to form a shift mode counter. Their outputs, 1514 and 1515, respectively, are decoded by BCD to decimal decoder 1516 which is connected to multiplexer circuit 1517. The output of decoder 1517 is 1518 which is used to clock flip-flops 1508 and 1509 which are connected as a shift counter and their respective outputs 1519 and 1520 address the input signals to data selector 1517.

The table in FIG. 15A illustrates the relationship between the output signals from counters 1506–1507 and 1508–1509. It can be seen that the two sets of signals are always different. It is apparent then, that coincidence between flip-flops 1501–1504 and flip-flops 1506–1507 and consequent selection of flip-flops 1508–1509 as a source of data to load into 1501–1504 insures that a different code will always result.

Signal 321 is a signal common to all five circuits typified by FIG. 15. Signal 1409 is typical of five different signals, one connected to each separate circuit. If these signals ae obtained from separate free running non-related oscillators a random relationship will exist between each of the five characters on a line. In practice, a pseudo random relationship has been found to be adequate. Therefore, in the exemplary embodiment, signals typified by 1409 were obtained from horizontal drive pulses. Propogation delays between the points selected for the five signals are sufficient to provide the required pseudo random relationship.

Figure 16:
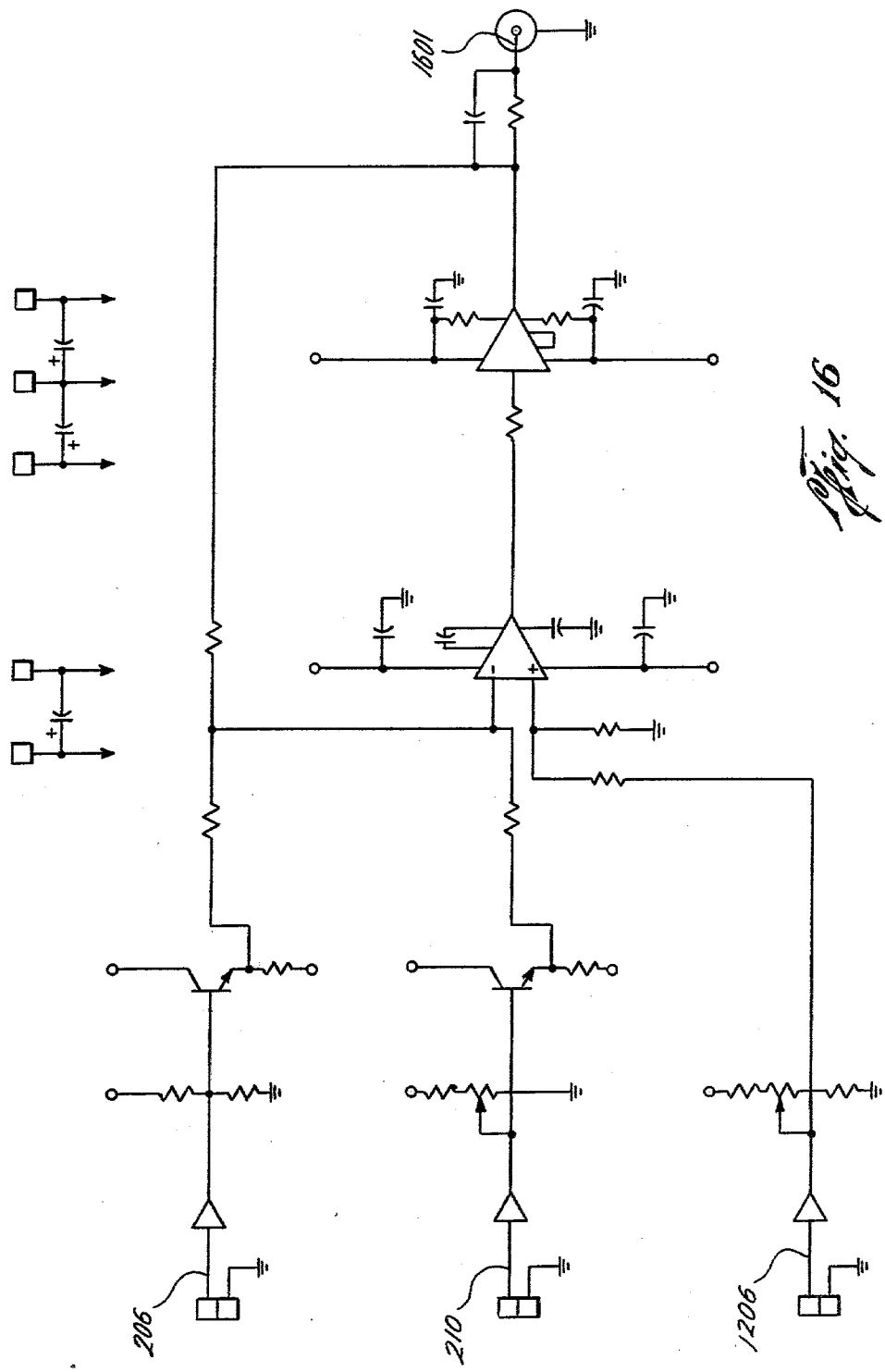
FIg. 16 is a schematic of conventional video driver circuits which deliver composite video signals to the video displays.
Figure 17:
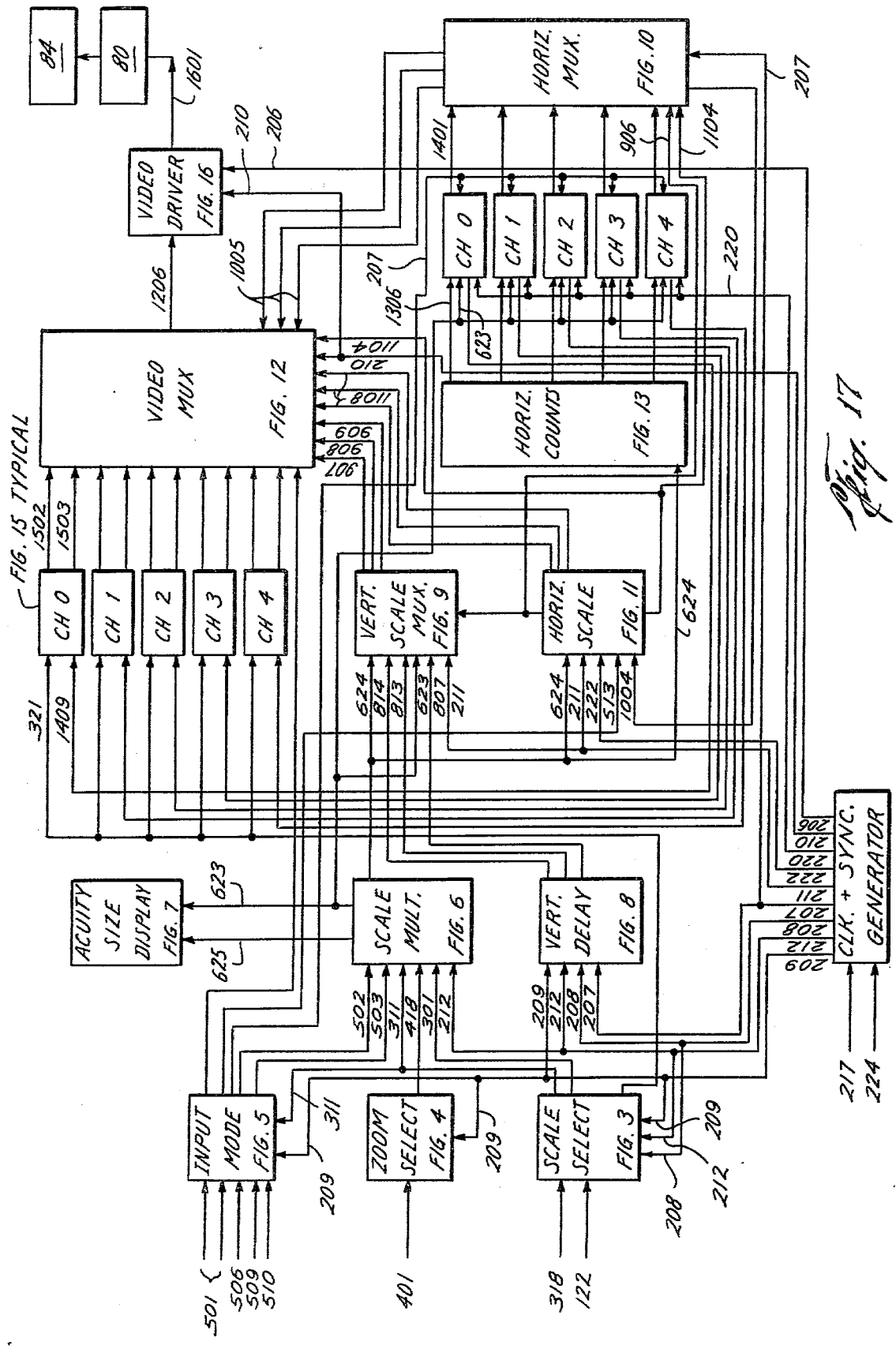
FIG. 17 is a detailed block diagram showing the various circuits interconnected.

FIG. 16 is a conventional video driver which mixes signals 1206, 206 and 210 to produce composite video signals 1601. Signal 1601 is used to drive video displays 80 and 84. The displays are viewed by the patient and the examiner.

The present invention, therefore, is well adapted to carry out the objects and attain the ends and advantages mentioned as well as others inherent therein. While the exemplary embodiments of the invention are given for the purpose of disclosure, numerous changes in the details of construction and arrangements of parts may be made which will readily suggest themselves to those skilled in the art and which are encompassed within the spirit of the invention and the scope of the appended claims.

What is claimed is:

1. An apparatus for generating and displaying visual acuity targets comprising,
   an electronic display device for displaying visual acuity testing targets,
   an electronic memory connected to said device containing a code for constructing a multiplicity of acuity targets for presentation to the display device,
   means connected to the memory for varying the size of said targets presented to the display device,
   means connected to the memory for presenting the targets in various orientations,
   control means for selective actuation of the size varying means and the orientation means, and
   means for varying the size of said targets includes means for varying the vertical and horizontal dimensions of the target about a single central point so target location does not change as size is varied.

2. An apparatus for generating and displaying visual acuity targets comprising,
   an electronic display device for displaying visual acuity testing targets,
   an electronic memory connected to said device containing a code for constructing a multiplicity of acuity targets for presentation to the display device,
   means connected to the memory for varying the size of said targets presented to the display device,
   means connected to the memory for presenting the targets in various orientations,
   control means for selective actuation of the size varying means and the orientation means, and means for zooming the size of said targets displayed on the display device in small increments.

3. An apparatus for generating and displaying visual acuity targets comprising,
an electronic display device for displaying visual acuity testing targets,
an electronic memory connected to said device containing a code for constructing a multiplicity of acuity targets for presentation to the display device,
means connected to the memory for varying the size of said targets presented to the display device,
means connected to the memory for presenting the targets in various orientations,
control means for selective actuation of the size varying means and the orientation means, and
a control and means connected to said memory for selectively presenting single or multiple targets on said display device.

4. An apparatus for generating and displaying visual acuity targets comprising,
an electronic display device for displaying visual acuity testing targets,
an electronic memory connected to said device containing a code for constructing a multiplicity of acuity targets for presentation to the display device,
means connected to the memory for varying the size of said targets presented to the display device,
means connected to the memory for presenting the targets in various orientations,
control means for selective actuation of the size varying means and the orientation means, and
means connected to said memory for selectively presenting normal or reverse video presentation to the display device.

5. An apparatus for generating and displaying visual acuity targets comprising,
an electronic display device for displaying visual acuity testing targets,
an electronic memory connected to said device containing a code for constructing a multiplicity of acuity targets for presentation to the display device,
means connected to the memory for varying the size of said targets presented to the display device,
means connected to the memory for presenting the targets in various orientations,
control means for selective actuation of the size varying means and the orientation means, and
means for locating the central points of multiple targets as a function of size.

6. An apparatus for generating and displaying visual acuity targets comprising,
an electronic display device for displaying visual acuity testing targets,
an electronic memory connected to said device containing a code for constructing a multiplicity of acuity targets for presentation to the display device,
means connected to the memory for varying the size of said targets presented to the display device,
means connected to the memory for presenting the targets in various orientations,
control means for selective actuation of the size varying means and the orientation means, and
means adjacent the control means for indicating the size of the target displayed on the display device.

7. An apparatus for generating and displaying visual acuity targets comprising,
an electronic display device for displaying visual acuity testing targets,
an electronic memory connected to said device containing a code for constructing a multiplicity of acuity targets for presentation to the display device,
means connected to the memory for varying the size of said targets presented to the display device,
means connected to the memory for presenting the targets in various orientations,
control means for selective actuation of the size varying means and the orientation means, and
a beam splitter positioned in front of the electro-optical device for minimizing the effects of ambient illumination.

8. An apparatus for generating and displaying visual acuity targets comprising,
first and second electronic display devices for displaying visual acuity testing targets, one of which is adapted to be viewed by a patient and the other of which is adapted to be viewed by an operator,
a memory connected to said devices and containing a code for constructing a multiplicity of acuity targets for presentation to the display devices,
means connected to the memory for varying the size of said targets presented to said display devices including means for varying each of the targets about its own center,
means connected to the memory for presenting the targets in various orientations,
means connected to the memory for selectively presenting single or multiple targets on said display devices, and
control means connected to and selectively actuating the size varying means, orientation means, and single or multiple target means.

9. The apparatus of claim 8 including,
means for zooming the size of said targets displayed on the display devices in small increments.

10. The apparatus of claim 8 including,
means for maintaining proportional spacing of multiple targets as the size of the targets varies.

11. The apparatus of claim 8 including,
means connected to said memory for selectively presenting normal or reverse video presentation to the display devices.

12. The apparatus of claim 8 including,
means adjacent the control means for indicating the size of the target displayed on the display devices.

13. A visual acuity testing device comprising,
an operator's console containing a video display and operating controls for the system,
a patient's video display,
an electronics module having a code memory for constructing a multiplicity of acuity testing target characters in various orientations,
said electronics module also containing the circuitry to generate and control the acuity target sizes digitally and about their own respective centers on said video displays, and
switch means are provided for selecting one of a multiplicity of available target sizes, zoom increasing size or decreasing size controls, single or line of characters select, normal or reverse video presentation, and change character orientation pushbuttons.

14. A visual acuity testing device comprising,
an operator's console containing a video display and operating controls for the system,
a patient's video display,
an electronics module having a code memory for constructing a multiplicity of acuity testing target characters in various orientations,
said electronics module also containing the circuitry to generate and control the acuity target sizes digitally and about their own respective centers on said video displays, and
the electronics module includes means to subtract from top edge of the video display to center of target data to open a vertical window for beginning the character, said subtraction being the number of vertical lines to the center of character less one-half of the character height times the size scale.

15. The apparatus of claim 14 wherein said means counts the number of lines within each of the vertical segments of the target character in accordance with the requirements of the selected scale and closes the vertical window.

16. The apparatus of claim 15 wherein said counting sequence divides the total number of lines into the required number of lines for each of two fields in an interlaced vertical scan.

17. The apparatus of claim 16 wherein the vertical component of the zoom mode is effected by continually adjusting the data to the counters so as to move the edges and change the number of lines per segment of the vertical window.

18. A visual acuity testing device comprising,
an operator's console containing a video display and operating controls for the system,
a patient's video display,
an electronics module having a code memory for constructing a multiplicity of acuity testing target characters in various orientations,
said electronics module also containing the circuitry to generate and control the acuity target sizes digitally and about their own respective centers on said video displays, and
the operator's console includes a digital display showing the actual size of the acuity targets.

19. A visual acuity testing device comprising,
an operator's console containing a video display and operating controls for the system,
a patient's video display,
an electronics module having a code memory for constructing a multiplicity of acuity testing target characters in various orientations,
said electronics module also containing the circuitry to generate and control the acuity target sizes digitally and about their own respective centers on said video displays, and
the electronics module also includes means to subtract from left edge of video display to the center of the first and each subsequent character in a horizontal line of targets to open a horizontal window for beginning each character at its leftmost edge,
said subtraction being the number of counts to center of character less one-half of the character width times the size scale.

20. The apparatus of claim 19 wherein said means counts the number of counts of a horizontal drive clock within each of the horizontal segments of each character in accordance with the requirements of the selected scale and closes the horizontal window.

21. The apparatus of claim 20 wherein the horizontal component of the zoom mode is effected by adjusting continually data to the counters so as to move the edges and changing the numbers of counts per segments of the horizontal windows.

22. A visual acuity testing device comprising,
an operator's console containing a video display and operating controls for the system,
a patient's video display
an electronics module having a code memory for constructing a multiplicity of acuity testing target characters in various orientations,
said electronics module also containing the circuitry to generate and control the acuity target sizes digitally and about their own respective centers on said video displays,
the electronics module includes means to present the characters in a line, spaced apart at a distance which is a function of target size, and
said means deletes the outermost characters from the displays at larger scales in either a selected size or zoom mode for eliminating incomplete and distorted characters at the video edges.

23. A visual acuity testing device comprising,
an operator's console containing a video display and operating controls for the system,
a patient's video display,
an electronics module having a code memory for constructing a multiplicity of acuity testing target characters in various orientations,
said electronics module also containing the circuitry to generate and control the acuity target sizes digitally and about their own respective centers on said video displays, and
the electronics includes means to change the address of the characters in read only memories in response to the change orientation switch,
said means including circuitry which inhibits the current orientation and insures that a change in character orientation will always occur.

* * * * *